(12) United States Patent
Perreault

(10) Patent No.: US 7,531,632 B2
(45) Date of Patent: May 12, 2009

(54) CLARIFICATION OF TRANSGENIC MILK USING DEPTH FILTRATION

(75) Inventor: Mark A. Perreault, Leominster, MA (US)

(73) Assignee: GTC Biotherapeutics, Inc., Framingham, MA (US)

(*) Notice: Subject to any disclaimer, the term of this patent is extended or adjusted under 35 U.S.C. 154(b) by 0 days.

(21) Appl. No.: 11/355,557

(22) Filed: Feb. 16, 2006

(65) Prior Publication Data

US 2007/0192878 A1 Aug. 16, 2007

(51) Int. Cl.
*C07K 1/00* (2006.01)

(52) U.S. Cl. .................. 530/366; 530/412; 530/416; 530/418

(58) Field of Classification Search ................ 530/366, 530/412, 416, 418
See application file for complete search history.

(56) References Cited

U.S. PATENT DOCUMENTS

| | | | |
|---|---|---|---|
| 3,519,558 A | 7/1970 | Cooper et al. | |
| 3,757,005 A | 9/1973 | Kautz et al. | |
| 4,089,778 A | 5/1978 | Gauger | |
| 4,105,547 A | 8/1978 | Sandblom et al. | |
| 4,350,156 A | 9/1982 | Malchesky et al. | |
| 4,351,710 A | 9/1982 | Jain et al. | |
| 4,397,747 A | 8/1983 | Ikeda | |
| 4,420,398 A | 12/1983 | Castino | |
| 4,644,056 A | 2/1987 | Kothe et al. | |
| 4,789,482 A | 12/1988 | Dileo et al. | |
| 4,873,316 A | 10/1989 | Meade et al. | |
| 4,874,516 A | 10/1989 | Kondo | |
| 4,888,115 A | 12/1989 | Marinaccio et al. | |
| 4,971,670 A | 11/1990 | Faupel et al. | |
| 5,256,294 A | 10/1993 | van Reis et al. | |
| 5,356,651 A | 10/1994 | Degen et al. | |
| 5,490,937 A | 2/1996 | van Reis et al. | |
| 5,518,624 A | 5/1996 | Filson et al. | |
| 5,585,466 A | 12/1996 | Carter et al. | |
| 5,597,486 A | 1/1997 | Lutz | |
| 5,633,076 A | 5/1997 | DeBoer et al. | |
| 5,750,172 A | 5/1998 | Meade et al. | |
| 5,756,687 A | 5/1998 | Denman et al. | |
| 5,827,690 A | 10/1998 | Meade et al. | |
| 5,945,577 A | 8/1999 | Stice et al. | |
| 5,948,441 A | 9/1999 | Lenk et al. | |
| 6,054,051 A | 4/2000 | van Reis et al. | |
| 6,194,553 B1 | 2/2001 | Lee et al. | |
| 6,221,249 B1 | 4/2001 | van Reis et al. | |
| 6,268,487 B1 | 7/2001 | Kutzko et al. | |
| 6,387,270 B1 | 5/2002 | van Reis et al. | |
| 6,441,145 B1 * | 8/2002 | DiTullio et al. ............. 530/393 |
| 6,555,006 B2 | 4/2003 | van Reis et al. | |
| 6,593,463 B1 | 7/2003 | Chen et al. | |
| 6,984,378 B1 | 1/2006 | Conkle et al. | |
| 7,026,154 B1 * | 4/2006 | Gaillac et al. ............. 435/236 |
| 2002/0108907 A1 | 4/2002 | van Reis et al. | |
| 2003/0178367 A1 | 9/2003 | van Reis et al. | |
| 2003/0229212 A1 | 12/2003 | Fahrner et al. | |
| 2004/0162414 A1 | 8/2004 | Santora et al. | |
| 2004/0167320 A1 | 8/2004 | Couto et al. | |
| 2004/0171103 A1 | 9/2004 | Bradley et al. | |
| 2005/0029195 A1 | 2/2005 | Gibson et al. | |
| 2005/0197496 A1 | 9/2005 | Perreault et al. | |
| 2005/0260672 A1 | 11/2005 | Couto et al. | |
| 2006/0130159 A1 | 6/2006 | Masiello et al. | |

FOREIGN PATENT DOCUMENTS

| | | |
|---|---|---|
| EP | 0208450 | 1/1987 |
| EP | 0552192 | 3/1995 |
| GB | 2178742 | 2/1987 |
| WO | WO 85/03011 | 7/1985 |
| WO | WO 92/04970 | 4/1992 |
| WO | WO 93/21781 | 11/1993 |
| WO | WO 97/42835 | 11/1997 |
| WO | WO 99/51724 | 10/1999 |
| WO | WO 00/17239 | 3/2000 |
| WO | WO 00/48703 | 8/2000 |
| WO | WO 03/045996 * | 6/2003 |
| WO | WO 2007/106078 | 9/2007 |

OTHER PUBLICATIONS

Andersson, 1966, "The Heterogeneity of Bovine Serum Albumin," Biochim. Biophys. ACTA. 117:115-133.

Aranha-Creado H, and Fennington GJ Jr (1997), *Cumulative Viral Titer Reduction Demonstrated By Sequential Challenge Of A Tangential Flow Membrane Filtration System And A Direct Flow Pleated Filter Cartridge*, PDA J Pharm So Technol 51(5):208-212.

Aravindan GR, et al., (1997), *Identification, Isolation, and Characterization Of A 41 Kilodalton Protein From Rat Germ Cell-Conditioned Medium Exhibiting Concentration Dependent Dual Biological Activities*, Endocrinology 138(8):3259-68.

Baguisi A,(1999) et al., *Production of Goats by Somatic Cell Nuclear Transfer*, Nature Biotech; 17: 456-461.

(Continued)

*Primary Examiner*—Tekchand Saidha
(74) *Attorney, Agent, or Firm*—Wolf, Greenfiled & Sacks, P.C.

(57) ABSTRACT

Processes and apparati are provided for separating molecules of interest from a mixture by depth filtration (DF). The DF of the invention is useful in the clarification and processing of various feedstreams for the removal of a molecule of interest. According to a preferred embodiment, a transgenic milk feedstream is stabilized and particulate matter such as fat, casein miscelles and bacteria are removed. An aseptic filtration step was also developed to remove any bacteria remaining in a clarified transgenic milk feedstream.

28 Claims, 15 Drawing Sheets

OTHER PUBLICATIONS

Borneman et al., Semi-continuous prtotein fractionation using affinity cross-flow filtration Desalination 144 (2002) 295-299.

Bracewell D.G. et al., (2004) *Addressing a Whole Bioprocess in Real-Time Using an Optical Biosensor-Formation, Recovery and Purification of Antibody Fragments From a Recombinant E. coli Host*, Bioprocess Biosyst Eng. Jul. 2004; 26(4):271-82. Epub May 5, 2004.

Chang et al., A carboxyl-terminal fragment of Plasmodium falciparum gp195 expressed by a recombinant baculovirus induces antibodies that completely inhibit parasite growth. J Immunol. Jul. 15, 1992; 149(2):548-55.

Charlton H.R., et al., (1999) *Characterization of a Generic Monoclonal Antibody Harvesting System for Adsorption of DNA by Depth Filters and Various Membranes*, Bioseparation. 8(6):281-91.

Cheryan, M. Ultrafiltration handbook Technomic Publishing Company Inc. (Lancaster), pp. 2-5.

Christy C., et al., (2002) *High Performance Tangential Flow Filtration: A Highly Selective Membrane Separation Process*, Desalination, vol. 144: 133-36.

De Jonge, E. et al., (1993), *Filtration Processes in the Cohn Fractionation Process*. Biotechnol Blood Proteins, 227:49-54.

Diggs et al., The major merozoite surface protein as a malaria vaccine target. Parasitol Today. Aug. 1993;9(8):300-2.

Dutta et al., Purification, characterization, and immunogenicity of a disulfide cross-linked Plasmodium vivax vaccine candidate antigen, merozoite surface protein 1, expressed in *Escherichia coli*. Infect Immun. Sep. 2001;69(9):5464-70.

Federspiel G, et al., (1991), *Hybridoma Antibody Production In Vitro In Type II SerumFree Medium Using Nutridoma-SP Supplements: Comparisons With In Vivo Methods*, J Immunol Methods 145(1-2):213-221.

Fox, P.F. and McSweeny, P.L.H. Dairy and Biochemistry. New York, New York: Plenum Publishers, 1998. p. 2.

Gabler et al., (1987), *Principles of Tangential Flow Filtration: Applications to BiologicalProcessing*, in Filtration in the Pharmaceutical Industry, pp. 453-490.

Genovesi, "Several Uses for Tangential-Flow Filtration in the Pharmaceutical Industry", 1983; J. Pharenter. Aci. Technol. 37(3):81-86.

Ghosh R, et al., (2003) *Parameter Scanning Ultrafiltration: Rapid Optimisation of Protein Separation*, Biotechnol Bioeng., Mar. 20;81(6):673-82.

Groner, A., Schmitt, K., and Schuler, E. (1999) Elimination of parvovirus B19 by the manufacturing process of Kybernin P. Ann. Hematol. 78 (Suppl. 1):A90.

Hossner et al., "Improved recovery of insulin-like growth factors (IGFs) from bovine colostrum using alkaline diafiltration", Biotechnol Appl Biochem. Dec. 2000;32 (Pt 3):161-6.

Kahn DW, et al., (2000), *Purification Of Plasmid DNA By Tangential Flow Filtration*, Biotechnol Bioeng. 69(1):101-106.

Kawahara H, et al., (1994), *High-Density Culture of FM-3A Cells Using a Bioreactor With An External Tangential-Flow Filtration Device*, Cytotechnology 14(1):61-66.

Kersten, Protein fractionation using the membrane filtration method. Chemical Abstracts. Database Accession No. 136:246645.

Koros, W.J. et al., (1996), *Terminology for Membranes and Membrane Processes* (IUPAC Recommendations 1996). Pure & Appl. Chem. 68:1479-89.

Lee et al., "Preparative HPLC" 8th International Biotechnology Symposium—Proceedings 1:593-610 (1988).

Lee et al., Effects of solutes on solubilization and refolding of proteins from inclusion bodies with hihg hydrostatic pressure (2006) Protein Science 15: 304-313 (abstract only).

Michaels, "Fifteen Years of Ultrafiltration: Problems and Future Promises of an Adolescent Technology", Ultrafiltration Membranes and Applications, Polymer Science and Technology, 13 (Plenum Press, N.Y., 1979, Anthony R. Cooper, ed., ) pp. 1-19.

Millesime L, et al., (1996) *Fractionation of Proteins with Modified Membranes*, Bioseparation, Jun;6(3):135-45.

Morcol et al., *Model Process for Removal of Casein from Milk of Transgenic Animals*, Biotechnol. Prog. 17:577-82 (2001).

Morgan AJW, and Pickup RW (1993), *Activity Of Microbial Peptidases, Oxidases, And Esterases In Lake Waters Of Varying Trophic Status*, Can J Microbiol 39(8):795-803.

Olsen et al. Separations Technology Pharmaceutical and Biotechnology Applications (Wayne P. Olsen) editor, Interpharm Press 1995.

Prado SM, et al., (1999), *Development and Validation Study for the Chromatographic Purification Process for Tetanus Anatoxin on Sephacryl S-200 High Resolution*, Boll Chem Farm. 138(7):364-368.

Porter, ed., Handbook of Industrial Membrane Technology, (Noyes Publications, Park Ridge, New Jersey, (1998) pp. 160-176.

Punidadas et al., Separation of milk proteins into fractions rich in casein or why proteins by cross flow filtration. Food Research International. 1998;31(4):265-72.

Quirk, et al., "Investigation of the parameters affecting the separation of bacterial enzymes from cell debris by tangential flow filtration", 1984; Enzyme Microb. Technol., 6(5):201.

Ramachandra-Rao, H.G. et al., (2002) *Mechanisms of Flux Decline During Ultrafiltration of Dairy Products and Influence of pH on Flux Rates of Whey and Buttermilk*, Desalination, vol. 144: 319-24.

Reynolds, T. et al., (2003) *Scale-Down of Continuous Filtration for Rapid Bioprocess Design: Recovery and Dewatering of Protein Precipitate Suspensions*, Biotechnol. Bioeng. Aug. 20;83(4):454-64.

Ronco C, et al., (1994), *On-Line Filtration of Dialysate: Structural And Functional Features Of An Asymmetric Polysulfone Hollow Fiber Ultrafilter*, Int J Artif Organs 17(10):515-520.

Stowers et al., Efficacy of two alternate vaccines based on Plasmodium falciparum merozoite surface protein 1 in an Aotus challenge trial. Infect Immun. Mar. 2001;69(3):1536-46.

Strauss PR (1995), *Use Of Filtron Mini- Ultrasette Tangential Flow Device And Filtron Microset Centrifugal Concentrators In The Early Stages Of Purification Of DNA Polymerases* Biotechniques 18(1):158-160.

Van Holten R.W. et al., (2003), *Evaluation of Depth Filtration to Remove Prion Challenge from an Immune Globulin Preparation*, Vox Sang. Jul;85(1):20-4.

Van Reis R., and Zydney., Membrane Separations in Biotechnology, Curr Opin Biotechnol., Apr. 2001; 12(2):208-11.

Van Reis R., et al., *High Performance Tangential Flow Filtration*, Biotech. Bioeng., 56: 71-82, (1997).

Wan et al. High-resolution plasma protein fractionation using ultrafiltration Desalination 144 (2002) 301-306.

Wilmut I, et al., (2002) *Somatic Cell Nuclear Transfer*, Nature 10;419(6907):583-6.

Wilmut I, et al., (1997) *Viable Offspring Derived From Fetal and Adult Mammalian Cells*, Nature Feb. 27;385(6619):810-3.

Zeman, L.J. & Zydney, A.L. (1996), *Microfiltration and Ultrafiltration* in Principles and Applications. (Marcel Dekker ed.), New York. p. 11.

Zou X, et al.,(2002) Generation of Cloned Goats (*Capra hircus*) from Transfected Foetal Fibroblast Cells, The Effect of Donor Cell Cycle, Mol Reprod Dev.; 61: 164-172.

\* cited by examiner rhAT Depth Filtration

1. MW Std
2. Blank
3. Whole Milk Diluted 1:1
4. Blank
5. 500K Permeate
6. 0.1μm Pall Dual TFF
7. A.S. Depth Filtration
8. A.S. Depth Filtration (pH 4.0)

rhAT Depth Filtration

1. MW Std
2. 500K Permeate
3. Hep. Elu
4. A.S. Depth Filtration (Control - 4C)
5. Hep. F.T.
6. Hep. Wash
7. Hep. Elution h2
8. A.S. Depth Filtration (10hr - 60C)
9. Hep. F.T.
10. Hep. Wash
11. Hep. Elution h3

CLARIFICATION OF TRANSGENIC MILK USING DEPTH FILTRATION

FIELD OF THE INVENTION

The present invention provides an improved method and system of purifying specific target molecules from contaminants found in an initial feedstream. More specifically, the methods of the current invention provide for the processing of a sample solution through an improved method of depth filtration that enhances the purification, clarification and fractionation of a desired molecule from a given source material.

BACKGROUND OF THE INVENTION

The present invention is directed to improved methods and apparati for the production of proteins of interest from a given source material. It should be noted that the production of large quantities of relatively pure, biologically active molecules is important economically for the manufacture of human and animal pharmaceutical formulations, proteins, enzymes, antibodies and other specialty compounds. In the production of many polypeptides, antibodies and proteins, various recombinant DNA techniques have become the method of choice since these methods allow the large scale production of such proteins. The various "platforms" that can be used for such production include bacteria, yeast, insect or mammalian cell cultures as well as transgenic plants or animals. For transgenic animal systems, the preferred animal type is production in dairy mammals, but the transgenics platform technology also contemplates the use of avians or other animals to produce exogenous proteins, antibodies, or fragments or fusions thereof.

Producing recombinant proteins involves transfecting host cells with DNA encoding the protein of interest and growing the host cells, transgenic animals or plants under conditions favoring expression of the recombinant protein or other molecule of interest. The prokaryote—*E. coli* has been a favored cell culture host system because it can be made to produce recombinant proteins in high yields. However, *E. coli* are often unable to produce complex or large molecules with proper tertiary folding and resulting in lower or aberrant biological activity.

With improvements in the production of exogenous proteins or other molecules of interest from biological systems there has been increasing pressure on the biotechnology industry to develop new techniques to enhance the volume of production while simultaneously making it more efficient and cost effective in terms of the purification and product recovery. That is, with new products, and larger volumes of known products there is substantial interest in devising methods to bring these therapeutics, in commercial volumes, to market quickly. At the same time the industry is facing new challenges in terms of developing novel processes for the recovery of transgenic proteins and antibodies from various bodily fluids including milk, blood and urine.

Filtration technologies have been major tools in food processing for more than 25 years. The food preparation industry represents a significant part of the filtration and clarification industry world-wide. The main applications of filtration processes are in the dairy industry (whey protein concentration, milk protein standardization, etc.), followed by beverages (wine, beer, fruit juices, etc.) and egg products. Among the very numerous applications of the current invention on an industrial scale, the clarification of fruit, vegetable and sugar juices by microfiltration also allow the flow dynamics to be both simplified and to enhance the final product quality.

With large scale production it is typically the case that there are more complex problems. In addition, there are further challenges imposed in terms of meeting product purity and safety, notably in terms of virus safety and residual contaminants, such as DNA and host cell proteins that might be required to be met by the various governmental agencies that oversee the production of biologically useful pharmaceuticals.

Several methods are currently available to separate molecules of biological interest, such as proteins, from mixtures thereof. One important such technique is affinity chromatography, which separates molecules on the basis of specific and selective binding of the desired molecules to an affinity matrix or gel, while the undesirable molecule remains unbound and can then be moved out of the system. Affinity gels typically consist of a ligand-binding moiety immobilized on a gel support. For example, GB 2,178,742 utilizes an affinity chromatography method to purify hemoglobin and its chemically modified derivatives based on the fact that native hemoglobin binds specifically to a specific family of polyanionic moieties. For capture these moieties are immobilized on the gel itself. In this process, unmodified hemoglobin is retained by the affinity gel, while modified hemoglobin, which cannot bind to the gel because its poly-anion binding site is covalently occupied by the modifying agent, is removed from the system. Affinity chromatography columns are highly specific and thus yield very pure products; however, affinity chromatography is a relatively expensive process and therefore very difficult to put in place for commercial operations.

In both the biotech industry and in industry ultrafiltration has traditionally been used for size-based separation of protein mixtures wherein the ratio of the protein molecular masses have to be at least around 10 to 1. This has been a limiting factor in many industrial applications throughout industry and in particular in the recovery of biopharmaceuticals in the milk of transgenic mammals. Significant research has taken place in the optimization of ultrafiltration systems by altering the physiochemical conditions (i.e. pH and ionic strength) to achieve higher selectivities (Van Reis et al. (1997)).

More specifically, depth filtration (DF) and tangential flow microfiltration (MF TFF) are two widely adopted filtration techniques that are related, but differ in their manipulation of functional flow mechanics. Generally, in DF processes, the feedstream is preferably introduced perpendicular to the membrane surface. Substances smaller than the membrane pores can become trapped either on the membrane's surface or within the membrane matrix, whereas the filtrate passes through the membrane. Sometimes referred to as "dead-end" or "depth" filtration, DF is commonly used in applications such as clarification, prefiltration, sterile filtration and virus removal. Additionally the majority of depth filters used in the pharmaceutical industry are disposable in nature.

Alternatively, with MF TFF processes, the feedstream is introduced parallel to the membrane surface, resulting in a continuous sweeping of the filtration source material. Under optimal conditions, substances smaller than the membrane's pores escape as filtrate or permeate, and larger particles are retained as retentate. Because of MF TFF's sweeping action and cross-flowing process stream, TFF-based techniques are less prone to fouling than the DF processes of the invention, in which separated particles can accumulate either on or in the membrane. TFF systems exhibit predictable performance characteristics, reliability, and ability to process "difficult" feed streams—all of which have contributed to establishing this platform as the preferred separation method for many biopharmaceutical applications. TFF systems and membranes are not disposable, membranes are cleaned between batches and reused. For these reasons MF TFF systems are frequently used to separate small molecules (1-1000 kD) from larger particulates (1 um-10 um). However, the energy and cleaning associated with the use of MF TFF can often make its use in large volume enterprises impractical.

As mentioned, purifying a recombinant protein from milk is technically complex and expensive. The purification process must be reproducible, involving as few labor-intensive steps as possible, and maximize the yield of the target protein as measured by its biological activity. An ideal purification process optimizes yield, keeping manufacturing costs low.

Clearly then, there remains a need for the development of additional large scale processes for the optimal purification of proteins out of transgenic milk or host cell culture systems which address the relevant quantitative and qualitative issues. The present invention addresses and meets these needs by disclosing a purification process which, in part, relies upon a selective precipitation and depth filtration step which facilitates removal of vast quantities of contaminating/impure compounds, enhancing effectiveness, reducing cost and speeding up processing from a given feedstream.

According to the methods of the current invention improvements have been made to optimize conditions in order to increase the potential size exclusion properties. Various particulates in milk, such as casein and fat, are micelles. These micelles can be manipulated by buffer conditions and be forced to increase or decrease in size. This manipulation of buffer is used to increase the separation efficiency of the depth filtration process. These processes make possible the development of high-performance depth filtration (DF) from various feedstreams including milk. One molecule of interest that can be purified from a cell culture broth or a transgenic milk feedstream is human recombinant antithrombin. Other molecules of interest include without limitation, human albumin, alpha-1-antitrypsin, antibodies, Fc fragments of antibodies and fusion molecules wherein a human albumin protein acts as the carrier molecule. The resulting DF system is employed through the current invention to improve clarification and fractionation efforts even from the levels achieved by TFF.

SUMMARY OF THE INVENTION

Figure 1:
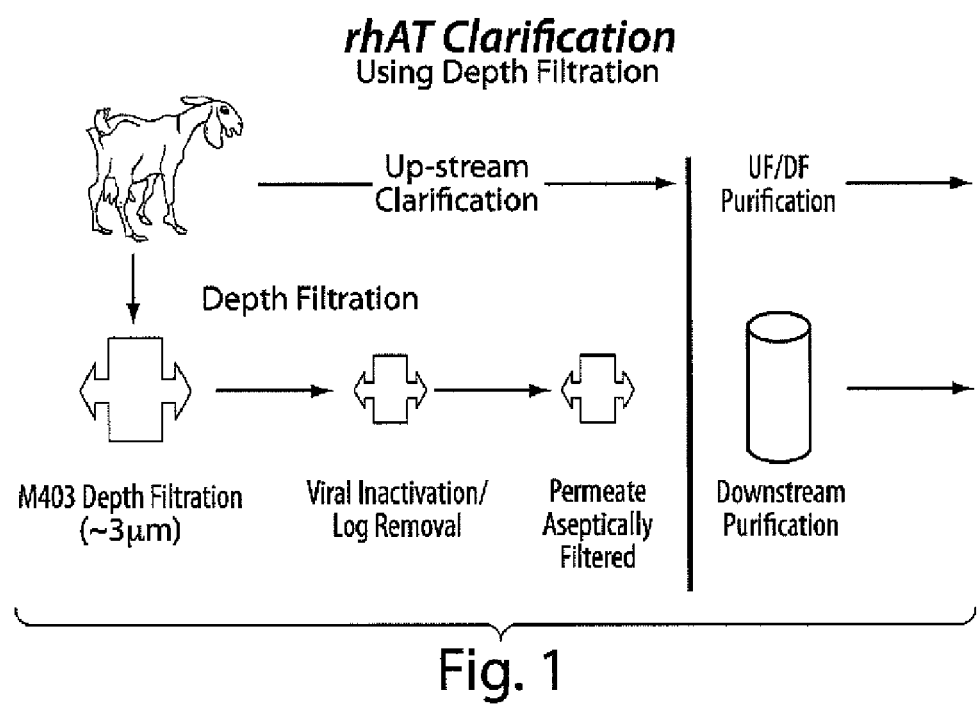
FIG. 1 Shows the Processing of rhAT according to the Depth Filtration techniques of the invention.
Figure 2A:
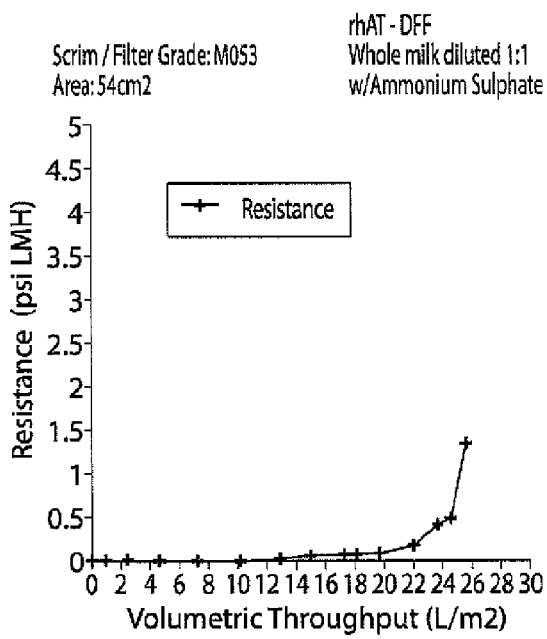
FIGS. 2A-2D Show the Volumetric Throughput versus Resistance of the current invention for a feed stream of interest.
Figure 2B:
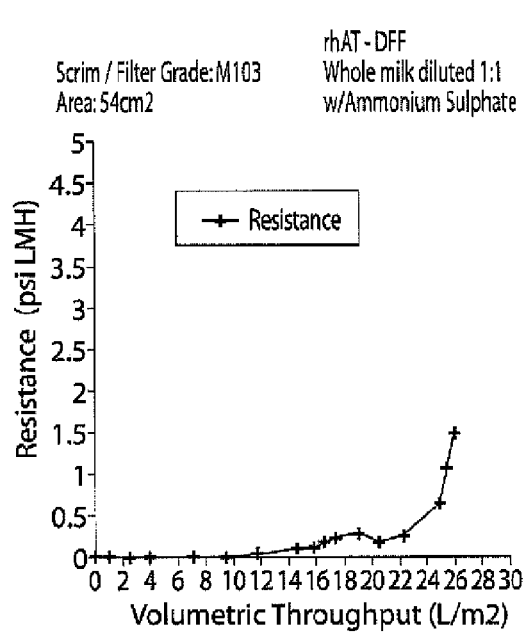
Figure 2C:
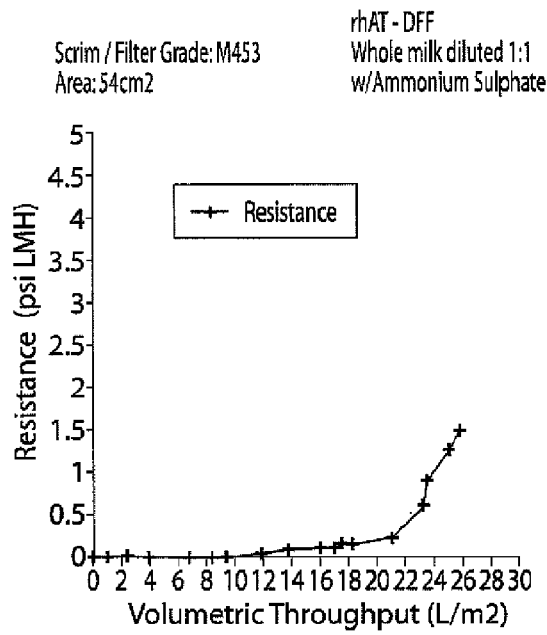
Figure 2D:
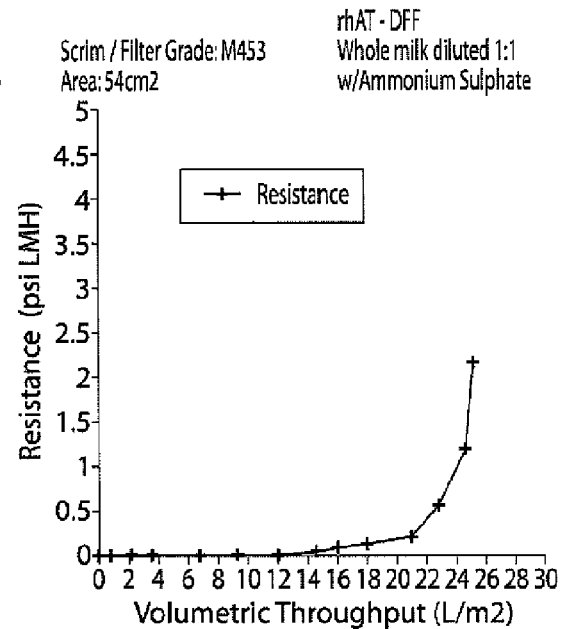

Briefly stated, the objective of the current invention is to use Depth Filtration (DF) techniques to achieve enhanced clarification and fractionation of a protein of interest. That is, to improve the separation efficiencies of a protein of interest from an initial feedstream using DF. More specifically, it is an object of the present invention to provide a depth filtration method and a series of reactants that substantially increase the effectiveness of such filtering activity from milk or cell culture fluid as a starting feedstream.

One protein of interest, and used as an example herein, is recombinant human antithrombin. The goal of the methods of the current invention are to pass the target protein, recombinant human antithrombin (rhAT) and retain the major contaminating milk proteins in the most efficient manner possible. According to the current invention, contaminating milk proteins include IgG, Lactoferrin, albumin, casein, lactoglobulin, and lactalbumin which are removed from a clarified bulk protein of interest. The methods of the current invention use rhAT as an exemplar but can be used for other proteins of interest.

Therefore, in a preferred embodiment of the current invention the filtration technology developed and provided herein provides a process to clarify and fractionate the desired recombinant protein or other molecule of interest from the native components of milk or contaminants thereof. The resulting clarified bulk intermediate is a suitable feed material for traditional purification techniques such as chromatography which are used down stream from the DF process to bring the product to a final formulation and purity useful for medicinal applications.

A preferred protocol of the current invention employs three filtration unit operations that clarify and fractionate the product from a given transgenic milk volume containing a molecule of interest. The clarification step removes larger particulate matter, such as fat globules and casein micelles from the product. The concentration and fractionation steps thereafter remove most small molecules, including lactose, minerals and water, to increase the purity and reduce the volume of the resulting product composition. The product of the DF process is tailor concentrated to a level suitable for optimal down stream purification and overall product stability. This clarified product is then aseptically filtered to assure minimal bioburden and enhance stability of the product for extended periods of time. The bulk product will realize a purity between 65% and 85% and may contain components such as albumin, whey proteins (β Lactoglobulin, αLactalbumin, and BSA), and low levels of residual fat and casein. This partially purified product is an ideal starting feed material for conventional down stream chromatographic techniques.

Typical of the products that the current invention can be used to process are other transgenically produced recombinant proteins of interest, including without limitation: antithrombin, rhAT, IgG1 antibodies, fusion proteins (ex: erythropoietin—human albumin fusion—"HEAP" or Human Albumin—Erythropoietin; or, a β-Interferon—rhAT), alpha-1-antitrypsin, IgG4, IgM, IgA, Fc portions, fusion molecules containing a peptide or polypeptide joined to a immunoglobulin fragment. Other proteins that can be processed by the current invention include recombinant proteins, exogenous hormones, endogenous proteins or biologically inactive proteins that can be later processed to restore biological function. Included among these processes, without limitation, are human growth hormone, antichymotrypsin, recombinant human albumin, decorin, human urokinase, tPA and prolactin.

Moreover, according to the current invention the alterations in salt (Ammonium Sulfate or EDTA) concentration differ from the prior art and serve to enhance the purity available according to those using the methods of the current invention.

According to additional embodiments of the current invention the DF techniques provided herein are applicable to a variety of different industries. In the beer industry, recovery of maturation and fermentation tank bottoms is already applied at industrial scale. During the last decade significant progress has been made with microfiltration membranes in rough beer clarification. The techniques of the current invention may be applicable in these efforts. Relative to wine improved filtration technologies will provide for improved microbiological and tartaric stability. In the milk and dairy industry, bacteria removal and milk globular fat fractionation using enhanced DF microfiltration techniques for the production of drinking milk and cheese milk are also useful.

It is an object of the present invention to provide more efficient depth filtration processes for separating species such as particles and molecules by size, which processes are selective for the species of interest, resulting in higher-fold purification thereof.

It is another object to provide improved filtration processes, including depth filtration processes, for separating biological macromolecules, such as proteins, from contaminating particles, such as fat and casein micelles, which causes pore fouling and flux decay.

These and other objects will become apparent to those skilled in the art. Other features and advantages of this invention will become apparent in the following detailed description of preferred embodiments of this invention, taken with reference to the accompanying drawings.

DESCRIPTION OF THE PREFERRED EMBODIMENT

The following abbreviations have designated meanings in the specification:

| Abbreviation Key: | |
|---|---|
| BSA | Bovine Serum Albumin |
| CHO | Chinese Hamster Ovary cells |
| CV | Crossflow Velocity |
| DF | Depth Filtration |
| DV | Diafiltration Volume |
| IEF | Isoelectric Focusing |
| GMH | Mass Flux (grams/m$^2$/hour) - also $J_M$ |
| LMH | Liquid Flux (liters/m$^2$/hour) - also $J_L$ |
| LPM | Liters Per Minute |
| M | Molar |
| MF | Microfiltration |
| NMWCO | Nominal Molecular Weight Cut Off |

| -continued | |
|---|---|
| Abbreviation Key: | |
| NWP | Normalized Water Permeability |
| PES | Poly(ether)-sulfone |
| pH | A term used to describe the hydrogen-ion activity of a chemical or compound according to well-known scientific parameters. |
| PPM | Parts Per Million |
| SDS-PAGE | SDS (sodium dodecyl sulfate) Poly-Acrylamide Gel electrophoresis |
| SEC | Size Exclusion Chromatography |
| TFF | Tangential Flow Filtration |
| PEG | Polyethylene glycol |
| TMP | Transmembrane Pressure |
| UF | Ultrafiltration |

Explanation of Terms

Clarification

The removal of particulate matter from a solution so that the solution is able to pass through a 0.2 μm membrane.

Colloids

Refers to large molecules that do not pass readily across capillary walls. These compounds exert an oncotic (i.e., they attract fluid) load and are usually administered to restore intravascular volume and improve tissue perfusion.

Concentration

The removal of water and small molecules with a membrane such that the ratio of retained molecules to small molecules increases.

Concentration Polarization

The accumulation of the retained molecules (gel layer) on the surface of the membrane caused by a combination of factors: transmembrane pressure, crossflow velocity, sample viscosity, and solute concentration.

Darcy's Law

An empirical law that governs flow through a porous media and also describes the relationship among flow rate, pressure drop, and resistance. Filter aid products are usually processed to provide a range of filtration rates that are closely related to permeability as reported in Darcy units.

Depth Filtration

A treatment process in which the entire filter bed is used to trap insoluble and suspended particles in its voids as water flows through it. The three dimensional sample collection patch may include a material capable of providing depth filtration or sieve filtration of a sample. Capacity is determined by the depth of the matrix. In depth filtration, particulates are trapped both within the matrix and on the surface of the filtration medium.

Diafiltration

A fractionation process of washing smaller molecules through a membrane, leaving the larger molecule of interest in the retentate. It is a convenient and efficient technique for removing or exchanging salts, removing detergents, separating free from bound molecules, removing low molecular weight materials, or rapidly changing the ionic or pH environment. The process typically employs a microfiltration membrane that is employed to remove a product of interest from a slurry while maintaining the slurry concentration as a constant.

Feedstream
The raw material or raw solution provided for a process or method and containing a protein of interest and which may also contain various contaminants including microorganisms, viruses and cell fragments. A preferred feedstream of the current invention is transgenic milk containing a exogenous protein of interest.

Filter Cake
Retained solids and filter media on the filter element.

Filtrate Flux (J)
Represents the rate at which a portion of the sample has passed through the membrane.

Flow Velocity (V)
The speed at which the fluid passes the surface of the membrane is considered the fluid flow velocity. Product flux will be measured as flow velocity is varied. The relationship between the two variables will allow us to determine an optimal operational window for the flow.

Fractionation
The preferential separation of molecules based on a physical or chemical moiety.

Gel Layer
The microscopically thin layer of molecules that can form on the top of a membrane. It can affect retention of molecules by clogging the membrane surface and thereby reduce the filtrate flow.

Membrane Pore Size Rating (MPSR)
A membrane pore size rating, typically given as a micron value, indicates that particles larger than the rating will be retained by the membrane.

Nominal Molecular Weight. Cut Off (NMWCO)
The size (kilodaltons) designation for the ultrafiltration membranes. The NMWCO is defined as the molecular weight of the globular protein that is 90% retained by the membrane.

Nominal Molecular Weight Limits (NMWL)
A membrane rating system that indicates that most dissolved macromolecules with molecular weights higher than the NMWL and some with molecular weights lower than the NMWL will be retained by the membrane in question.

Normalized Water Permeability (NWP)
The water filtrate flow rate established at a specific recirculation rate during TFF device initial cleaning. This value is used to calculate membrane recovery.

Microfiltration
Microfiltration is a pressure-driven solid-liquid separation process. According to the invention, microfiltration techniques are capable of removing suspended solids in the 0.10-1.0 micron range. In comparison, ultrafiltration is generally used with solids in the 0.01-0.10 micron range.

Molecule of Interest
Particles or other species of molecule that are to be separated from a solution or suspension in a fluid, e.g., a liquid. The particles or molecules of interest are separated from the fluid and, in most instances, from other particles or molecules in the fluid. The size of the molecule of interest to be separated will determine the pore size of the membrane to be utilized. Preferably, the molecules of interest are of biological or biochemical origin or produced by transgenic or in vitro processes and include proteins, peptides, polypeptides, antibodies or antibody fragments. Examples of preferred feedstream origins include mammalian milk, mammalian cell culture and microorganism cell culture such as bacteria, fungi, and yeast. It should also be noted that species to be filtered out include non-desirable polypeptides, proteins, cellular components, DNA, colloids, mycoplasm, endotoxins, viruses, carbohydrates, and other molecules of biological interest, whether glycosylated or not.

Precoat
A precoat is a thin layer, typically between 1.5 to 3.0 mm, of a filter aid that is applied to the septum before the actual filtration process. A precoat is usually unnecessary when using a depth filter as the septum Tangential Flow Filtration
A process in which the fluid mixture containing the components to be separated by filtration is re-circulated at high velocities tangential to the plane of the membrane to increase the mass-transfer coefficient for back diffusion. In such filtrations a pressure differential is applied along the length of the membrane to cause the fluid and filterable solutes to flow through the filter. This filtration is suitably conducted as a batch process as well as a continuous-flow process. For example, the solution may be passed repeatedly over the membrane while that fluid which passes through the filter is continually drawn off into a separate unit or the solution is passed once over the membrane and the fluid passing through the filter is continually processed downstream.

Recovery
The amount of a molecule of interest that can be retrieved after processing. Usually expressed as a percentage of starting material or yield.

Retentate
The portion of the sample that does not pass through the membrane, also known as the concentrate. Retentate is being re-circulated during the TFF.

The biologics industry is becoming increasingly concerned with product safety and purity, as well as cost of goods. The use of DF, according to the current invention, is a rapid, cheaper and more efficient method for biomolecule separation. It can be applied to a wide range of biological fields such as immunology, protein chemistry, molecular biology, biochemistry, and microbiology.

It should also be noted that genetically engineered biopharmaceuticals are purified from a supernatant containing a variety of diverse host cell contaminants. Reversed-phase high-performance liquid chromatography (RP-HPLC) is another method that can be used for protein purification because it can efficiently separate molecular species that are exceptionally similar to one another in terms of structure or weight. Procedures utilizing RP-HPLC have been published for many molecules. McDonald and Bidlingmeyer, *"Strategies for Successful Preparative Liquid Chromatography"*, PREPARATIVE LIQUID CHROMATOGRAPHY, Brian A. Bidlingmeyer (New York: Elsevier Science Publishing, 1987), vol. 38, pp. 1-104; Lee et al., *Preparative HPLC*. At the 8TH BIOTECHNOLOGY SYMPOSIUM, Pt. 1, 593-610 (1988). However, at commercial scale RP-HPLC is neither as cost-efficient nor as effective of the current invention.

The current invention provides the results of clarifying transgenic goat milk using "dead end" filtration or "depth filtration." Until the use of these specific buffer salts in milk, it could not be effectively clarified using DF because the size of the casein micelle was too small to be retained by these coarse filters. Fine filters able to retain the casein were plugged rapidly and not able to be used effectively. According to a preferred embodiment of this invention the milk of a transgenic dairy animal, a goat, was purified to a clarified bulk material using depth filtration. Depth filtration's advantage over tangential flow filtration is that no recirculation is needed for process filtration. The liquid is simply pumped in through the system and the filtrate exits the designated filter downstream. The filter elements are then disposed of eliminating the need for cleaning of the filters. Additionally milk clarified using depth filtration is produced in a single pass as opposed to lengthy recirculation process required by tangential flow filtration or other filtration schemes. Similar uses of the embodiments of the current invention could also be applied to isolating a protein of interest from a cell culture feedstream.

Process Steps

Processing steps from transgenic mammals include the following:
1. Collection Milk collection from each animal
2. Dilute the milk 1:1 with 3.8 M Ammonium Sulfate
3. Perform depth filtration/0.2 um Aseptic filtration Collect Permeate The present invention particularly contemplates filter applications of a type wherein the filter media is generally not reusable but is discarded together with the particulate solids removed from the fluid being filtered. Since the particulate solids represent a necessary disposal component, the total amount of solids to be disposed of from the filtering application can best be minimized by reducing the amount of filter media accompanying the particulate solids, and/or increasing the amount of solids retained per unit volume of filter media.

For filter applications of the type referred to above, filter media has long been employed wherein relatively thin and open wet strength layers are arranged on opposite surfaces of the filter media. The relatively thin and open structure of the wet strength layers are desirable for permitting maximum flow of fluid to be filtered through the filter media. Typically, one or more layers of filter septum material have been arranged between the wet strength layers to achieve depth filtration as described above. Furthermore, the wet strength layers have typically been bonded to the filter septum material, preferably by binder or adhesive which is commonly sprayed onto a surface of the filter septum material. The wet strength layer is then pressed onto the filter septum material in order to bond the two layers together. Bonding of the layers is generally necessary to maintain continuity of the filter media, for example, when it is replaced in the filter apparatus. The wet strength layer, by itself, is typically quite open and presents very little interference to the flow of liquid to be filtered through the filter media. However, the manner in which binder is commonly applied to bond the wet strength layer to the filter septum material typically results in the binder itself being a much greater cause of blinding or flow reduction than the wet strength layer itself.

Basics of Depth Filtration

Generally, a depth filter media is one having substantial tortuous paths which are capable of receiving and retaining smaller particulate material upon and within the cross-section of the filter media itself. Preferably, the depth filter media is formed with a matrix of multi-directional fibers forming the tortuous passages so that they are capable of trapping and retaining the smaller particles. A depth filter media accomplishes filtration at least partly because fluid passing through the filter media is caused to change direction as it passes through the multi-directional fibers. This in turn causes very fine particulate material in the liquid to be deposited and retained in niches or crevices even though the particles may be smaller than the openings in the media.

A depth filtration process is provided herein to remove cell debris, insoluble contaminating milk proteins, fat, and nucleic acid precipitate. This step provides a convenient means to economically remove cell debris, contaminating proteins and precipitate. In choosing a filter or filter scheme it was necessary to ensure a robust performance in the event upstream changes or variations occur. Maintaining the balance between good clarification performance and step yield requires investigation of a large variety of filter types with varying internal media. Suitable filters may utilize cellulose filters, regenerated cellulose fibers, cellulose fibers combined with inorganic filter aids (e.g. diatomaceous earth, perlite, fumed silica), cellulose fibers combined with inorganic filter aids and organic resins, or any combination thereof, and polymeric filters (examples include but are not limited to nylon, polypropylene, polyethersulfone) to achieve effective removal.

Depth Filtration

Depth Filtration is a treatment process in which the entire filter bed is used to trap insoluble and suspended particles in its voids as water flows through it. The sample collection patch may include a material capable of providing depth filtration of a sample. In depth filtration, particulates are trapped both within the matrix and on the surface of the filtration medium. Depth filters are composed of random mats of metallic, polymeric, inorganic, or organic materials. Depth filters rely on the density and thickness of the mats to trap particulates and fluids, and generally retain large quantities of particulates or fluids within the matrices. Certain disadvantages of depth filters include media migration, which is the shifting of the filter medium under stress, and particulate unloading at high differential pressures. Advantages of depth filters include reduced cost, high throughputs, high volume-holding capacity, removal of a range of particle sizes, and high flow rates. The extract of intracellular molecules is then separated from the remaining insoluble slurry by depth filtration, for example, using diatomaceous earth in a plate and frame filter press.

With a depth filter media as contemplated by the present invention, the filter media has or forms passages throughout its matrix which are capable of trapping and retaining very small particles, preferably in the range of about 1-5 microns.

The compositions for filtrations vary. In rough filtration or large volume filtration applications loose media such as diatomaceous earth (body remnants of extinct animals called diatoms) and/or perlite (a ground volcanic glass), have been used as depth filter media in pressure leaf filters. In the past cellulose, asbestos or other synthetic fibers have been combined with such loose media or used as pre-coating materials to prevent migration of the filter aid particulates through the filter screen support. Porous cellulose fiber membranes, ceramic membranes, wet strength resin binders and dry strength resin binders have also been used.

In order to assure continued effectiveness of the depth filtration techniques of the invention, it is also important that the filter media remain open at its top surface or, in other words, that it not be blinded by components of the filter media itself such as the wet strength layer or an associated binder or by particulate material deposited from the liquid being filtered. The present invention novelty assures that the depth filter media remains open by avoiding the use of adhesive or wet strength material formed on the top surface of the filter media receiving the liquid to be filtered. Accordingly, it is particularly important to understand that depth filtration is accomplished by the filter septum layer of the present invention and that the top surface of the filter septum layer itself remains exposed for receiving the liquid to be filtered.

As for particle size, depth filtration is generally contemplated for purposes of the present invention to include applications where the minimum particulate size is about 50 microns or less, usually with a substantial portion of the particulate solids being smaller than 50 microns. More preferably, depth filtration is contemplated for the present invention where particulate solids have a minimum size in the range of about 1-25 microns. As will be apparent from the following description, the depth filter media of the present invention is particularly useful for removing a substantial portion of those particulate solids.

According to the invention, there are at least two important concepts cooperating to form the foundation of the current invention. The first involves disassociating the casein micelles in milk with EDTA and clarifying the feed stream with a depth filter. The second involves aggregating the casein micelles with ammonium sulfate and clarifying the milk using a depth filter. The technology is a new process that combines existing methods in a novel manner producing a favorable result. The use of depth filtration to clarify milk did not seem feasible until the milk was treated with a buffer to alter the state of the casein micelle. Preferred embodiments of the current invention can be made operational in a closed system with simple skid design greatly enhancing the ability of users to maintain Good Manufacturing Processes ("GMP") operations and/or the containment of bio-hazardous agents. The process is also quicker and less labor intensive. Typically, flux rates for the filtration are between 60-80 LMH and between 30-40 liters/m2 of milk can be processed in approximately 2 hours.

The resulting permeate consists of the clarified milk which contains various soluble milk proteins and the transgenic protein of interest. The resulting retentate (or cake layer) which consists of a suspension of insoluble proteins and fat may be washed or solubilized and passed through the depth filter for collection. The remaining cake layer contains the remaining insoluble components of milk which is usually discarded.

Filtration methods of the type contemplated by the present invention are performed in filtration apparatus. The filter apparatus is commonly referred to as a filter press and includes relatively movable filter plates. One of the filter plates is connected with an inlet for receiving fluid to be filtered. Typically, the fluid is a liquid and even more typically water or water based fluids containing particulate solids to be removed during the filtration process. The other filter plate is connected with an outlet for receiving fluid passing through the filter apparatus and having particulate solids removed. Thus, the filtered fluid may be disposed of or recycled for further use, depending upon the particular application in which the filter apparatus is employed.

For replacement of the filter media, the flow of fluid through the filter apparatus is temporarily interrupted, the filter assembly is voided of fluid and the filter plates are separated from each other. The filter media is then withdrawn from the filter apparatus. At the same time, a fresh surface portion of the filter media is drawn, for example, from the supply roll into the filter apparatus. At that time, the filter plates are again pressed into engagement with each other to capture and seal the fresh supply of filter media there between and the filtration operation continued with the flow of additional fluid from the source.

Suitable microfiber materials according to the present invention include glass, polyester, polypropylene, polyethylene, nylon and other synthetic fibers having generally similar characteristics. It is generally believed that all of these synthetic fibers are available in both the short and long lengths described above. Typically, the synthetic fibers are relatively straight and round while normally resisting absorption of liquids because of their synthetic composition.

Once the precipitation is complete, depth filtration is conducted sequentially on each aliquot using the same filtration apparatus. It will become evident upon review of this specification that the processes of the present invention are scaleable, running the gamut from smaller scale (e.g., about 5-10 liter runs) all the way to commercial scale preparations, such as 1,000 to 5,000 L production runs. According to the current invention the process will be linearly scalable. The initial process steps (precipitation, depth filtration, and ultrafiltration) scale with feedstream volume while the anion exchange chromatography and subsequent steps scale with viral particle input.

Sterile filtration may be added to the current process to eliminate bioburden. The sterile filter may be constructed of a variety of other materials that are well known in the art and available to the artisan. These may include, but are not limited to, polypropylene, cellulose, regenerated cellulose, cellulose esters, nylon, polyethersulfone, or any other material which is consistent with low product binding. The filter may have a single membrane layer or may incorporate a prefilter of the same of different material. The product can be held frozen or at approximately 4° C. for subsequent formulation and filling.

According to another embodiment an orthogonal purification step may also be added to deal with impurity clearance, as well as an adventitious agent clearance step. Orthogonal purification steps are not necessarily required and may be assessed by the skilled artisan and in turn implemented based on need. Potential steps include flow-through cation exchange chromatography, reversed-phase adsorption, and hydroxyapatite chromatography. An anion exchange chromatography step also can be considered for removing additional impurities. This step can be operated in either bind/elute or flow-through modes. The step can be placed after either ultrafiltration step by ending the UF with a diafiltration into an appropriate buffer such as phosphate buffered saline (PBS).

According to the current invention a recombinant protein, rhAT, is selected for use in the development of new clarification techniques. This protein is expressed in transgenic milk that must be clarified prior to purification. Depth Filtration using depth filter media offers an attractive alternative to centrifugation or tangential flow filtration. It is simple to use, has low initial costs associated with set-up, and is disposable. The objective of milk clarification/aseptic filtration is to isolate the soluble components of milk, called whey proteins, and render a microbiologically stable product. The whey proteins include IgG, Lactoferin, Albumin, residual soluble Casein, Lactoglobulin, Lactalbumin, and the rhAT recombinant protein. The milk also contains particulate matter like fat globules, casein micelles and cell debris. Looking to FIG. 1, the particulates can be separated from the whey proteins, once the precipitation is complete, by passing them through a 5 μm depth filter.

According to a preferred embodiment of the current invention a critical step in clarifying a milk feedstream using depth filters is to partially precipitate the casein micelles using Ammonium Sulfate. In the presence of 1.9 M Ammonium Sulfate at pH 6.5, the casein begins to aggregate and the aggregate is easily retained by the more open depth filters. Additionally other less soluble milk proteins precipitate, IgG as an example is also removed using this method. Lastly, fat globules and cell debris are easily removed by the filter, yielding clarified whey proteins in the filtrate. According to the invention, the filtrate may then be aseptically filtered and stored at 4° C. prior to purification.

According to one embodiment of the current invention the DF techniques of the invention are provided followed by enhanced purification techniques leading to a pharmaceutical grade therapeutic composition that is bioactive. This process can be accomplished by further clarifying a DF fractionated feedstream by using a series of ion exchange chromatography columns. Such columns will preferably contain an exchange resin but may also provide for an affinity resin with contaminants being either captured on additional columns or washed away. The molecule of interest is then collected and prepared for delivery.

According to preferred embodiments of the current invention, DF processing runs were conducted using a 90 mm test cell and disk of filtration media. The initial experiments scouted four different grades of media ranging from 2.5 um up to 15 um in "pore size". Once an ideal grade of media was selected, the clarified milk was purified and used in the first stage of the purification process at a reduced scale. The results from this portion of the experiment confirm the technology is comparable to the more conventional clarified milk using tangential flow filtration.

Materials and Methods
Materials

| Description | Part Number |
| --- | --- |
| 90 mm Test Cell w/pressure gauge | M90 PD |
| Masterflex L/S Pump (10-600 RPM) | 07524-40 |
| Masterflex #14 Silicone Tubing | 96420-14 |
| Ertel Elsop Filter Media—2.5 um | M453 |
| Ertel Elsop Filter Media—5 um | M403 |
| Ertel Elsop Filter Media—10 um | M103 |
| Ertel Elsop Filter Media—15 um | M053 |
| 2 mm Scrim Pre-Filter | N/A |
| 3.8M Ammonium Sulfate, 0.2M Sodium Phosphate, | pH 6.5 |

Transgenic Goat Milk

Transgenic milk was separately collected from each of the transgenic goats and held at 4-8° C. until clarifying (<4 days unless noted).

| Goat Number | Collection Date | Storage Temp. |
| --- | --- | --- |
| G0881 | Aug.-Dec. 2005 | 4-8° C. |
| G0737 | Aug.-Dec. 2005 | 4-8° C. |
| C248 | Aug.-Dec. 2005 | 4-8° C. |
| C239 | Aug.-Dec. 2005 | 4-8° C. |
| B121 | Aug.-Dec. 2005 | 4-8° C. |

Clarification—Media Selection

Four separate clarification experiments were performed using Depth Filtration (DF) under similar operating parameters. The purpose of this experiment was to see the effect of different media grades on clarification. Initially 150 ml of milk was added to the sanitized feed reservoir and 150 ml of 3.8 M Ammonium Sulfate was added to the sanitized buffer reservoir of the microfiltration (MF) system. A dual head pump and static mixer was then used to mix the two streams in equal ratios. The mixture was then passed through the selected grade of media and the filtrate collected. The final clarified milk was aseptically filtered and stored in a PETG bottle at 4° C.

Analytical Methods
  Reverse Phase HPLC (RPC)
    Reverse phase chromatography was performed on each of the samples to evaluate the rhAT protein concentration isolated by this process step.
  SEC HPLC (RPC)
    Size exclusion chromatography was performed on each of the samples to evaluate the amount of rhAT monomer in each sample.
  Non Reduced SDS PAGE (RPC)
    SDS PAGE was performed on each of the samples to evaluate the clarified milk protein composition.

Results

Clarification—Media Selection

Clarification of rhAT transgenic milk was performed using different depth filter media between 2.5 um and 15 um under similar flow conditions. The pressure profiles for each run may be seen below in graphs 1-4. Starting in the upper left working down the page the results of throughput vs. resistance may be seen. As expected the resistance rises more quickly in the tightest grade of filter, M453 (2.5 um). The lowest resistance may be seen when using the M053 (15 um). Additionally the highest filtrate clarity was observed in the M453 (2.5 um) and the lowest in the M053 (15 um). All clarified milk samples were aseptically filtered using an 0.2 um syringe filter and the throughput recorded. As expected the clearest MF permeate had the highest throughput. It was for this reason that the M403 (5 um) grade filter was chosen as it had the best balance between clarity and throughput.

Milk Composition:

Cow milk is about 87% water, 4-5% fat, 5% carbohydrate, and 3-4% protein. Goat's milk and sheep's milk have lower fat content but higher protein content. Lactose is the major carbohydrate in the milk of most species—and the least variable component of milk. The fat component is a complex mixture of lipids secreted as globules primarily composed of a triglyceride surrounded by a lipid bilayer membrane, which helps to stabilize those fat globules in an emulsion within the aqueous environment of milk. More than 95% of total milk lipids are in the form of globules ranging from 0.1 to 15 μm in diameter. These liquid fat droplets are covered by a thin membrane, 8-10 nm thick, with properties completely different from both milk fat and plasma. The native fat globule membrane (FGM) is an apical plasma membrane of the secretory cell that continually envelopes the lipid droplets as they pass into the lumen. The major components of that native FGM, therefore, are protein and phospholipids. The major milk protein is casein. The principal casein fractions are (s1) and (s2) caseins, -casein, and -casein. The distinguishing property of all caseins is their low solubility at pH 4.6. A common compositional factor is that caseins are conjugated proteins, most with phosphate group(s) esterified to serine residues. Most if not all are found within a structure called a micelle. Its biological function is to carry large amounts of highly insoluble calcium phosphate to mammalian young in liquid form and to form a clot in the stomach for more efficient nutrition. Micelles are colloidal molecules with hydrophobic cores and casein-enriched surfaces held loosely together by calcium phosphate molecules. They form large aggregates with diameters of 90-150 nm. These aggregates are porous structures occupying about 4 mL/g and 6-12% of the total volume fraction of milk. The micelle structure also contains minerals, amino acids, and bioactive peptides.

Whey proteins also include a long list of enzymes, hormones, growth factors, nutrient transporters, and diseaseresistance factors. If the product protein tends to associate with either the fat or micelles, purification may be simplified, but this scheme is rare. Casein molecules can be separated from whey by precipitating out the casein with acid (a slow addition of 0.1-N HCl to lower the milk pH to 4.6) or by disrupting the micellar structure using partial hydrolysis of the protein molecules with a proteolytic enzyme such as chymosin. However, those methods can result in product losses as high as 40-60%, leading to significantly lower overall yields (5-25%) and low biological activity. In contrast salt solutions used in this method precipitate the casein micelles while not creating product loss provided that the protein of interest remains soluble.

Milk as a Feedstream

Milk may be the product of a transgenic mammal containing a biopharmaceutical or other molecule of interest. In a preferred embodiment the system is designed such that it is highly selective for the molecule of interest. The clarification step removes larger particulate matter, such as fat globules and casein micelles from the milk feedstream. The concentration/fractionation steps remove most small molecules, including lactose, minerals and water, to increased purity and reduce volume of the product. The product of the DF process is thereafter concentrated to a level suitable for optimal downstream purification and overall product stability. This concentrated product, containing the molecules of interest, is then aseptically filtered to assure minimal bio-burden (i.e., endotoxin) and enhance the stability of the molecules of interest for extended periods of time. According to a preferred embodiment of the current invention, the bulk product will realize a purity between 35% and 65% and may contain components such as goat antibodies (from transgenic goats), whey proteins ($\beta$ Lactoglobulin, $\alpha$ Lactalbumin, and BSA), as well as low levels of residual fat and casein. This partially purified product is an ideal starting feed material for conventional downstream chromatographic techniques to further select and isolate the molecules of interest which could include, without limitation, a recombinant protein produced in the milk, an immunoglobulin produced in the milk, or a fusion protein.

According to the current invention the objective of separating the protein of interest from contaminating proteins using DF is demonstrated. The goal of this clarification is to retain the fat, casein, and unwanted precipitated proteins while passing the soluble product and milk proteins. The RPC and SDS gel results conclusively show the contaminating milk components can be effectively reduced during the clarification. All but the product and soluble milk proteins are effectively removed using the 5 μm DF filter and methods of the invention.

Membrane Pore Size Rating (MPSR)

The DF pore size and milk buffer condition play a considerable role in the effectiveness of the clarification. Several DF pore sizes were evaluated including a 2.5 μm, 5.0 μm, 10 μm, and 15 μm. If the pore size is to low as in the case of the 2.5 μm, the throughput and flux are reduced, however, the clarity of the permeate was good. Each larger pore size was evaluated for its permeate quality, throughput and flux. The 2.5 μm, 5.0 μm, 10 μm filters all proved to retain the majority of the fat and precipitated milk components. The 15 μm filter could not efficiently be used for this filtration as the quality of the permeate was lower and a portion of the fat passed through the membrane creating a hazy permeate. The 5.0 μm filter showed the best throughput, flux, and permeate quality both initially and after being optimized. The pore size of this filter proved to be the largest size able to be used, yet still be able to retain the insoluble milk contaminants.

Turning to FIGS. 2A-2D, they demonstrate the Resistance of the filter and the volumetric throughput according to preferred embodiment of the invention.

Figure 3:
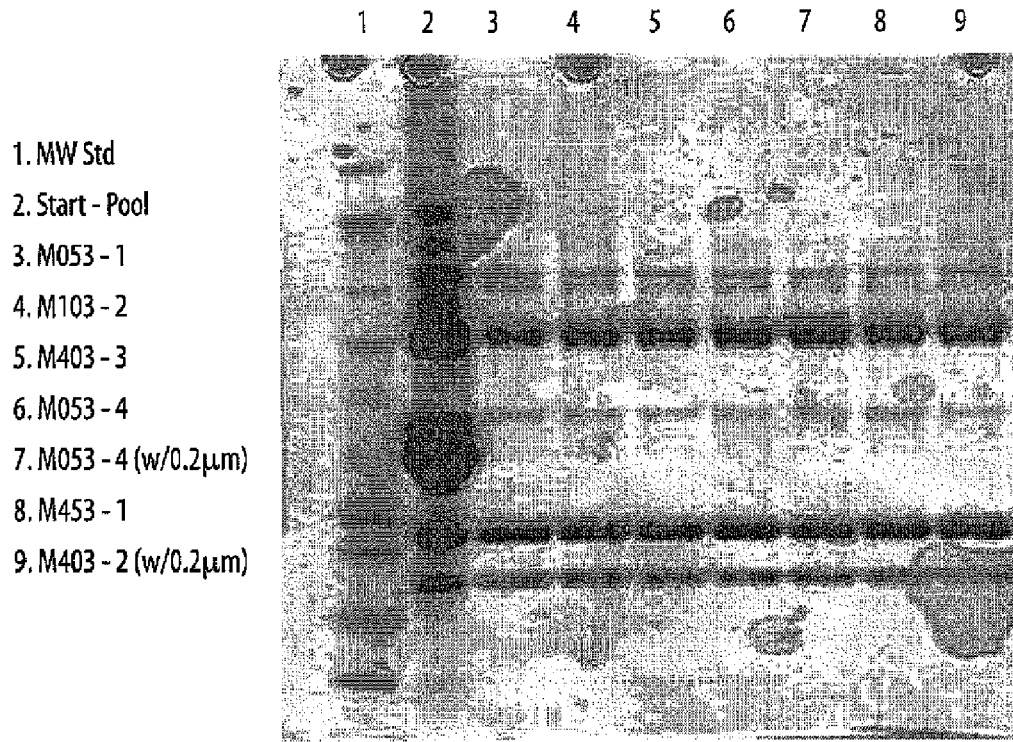
FIG. 3 Shows a non-reduced SDS page gel demonstrating the amount of rhAT recovery from a DF Matrix.

Turning to FIG. 3, it provides a non-reduced SDS page confirms the majority of rhAT is recovered in the filtrate of each of the experiments pursuant to the current invention. Also worth noting is the similarity between each of the filtrate streams (FIG. 3).

Clarification/Purification

Figure 4:
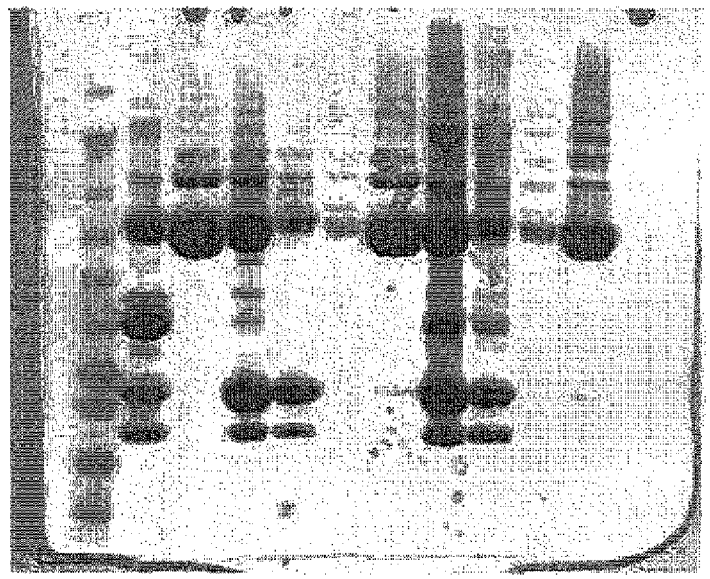
FIG. 4 Shows an SDS gel of rhAT recovery using a M403 (5 μm) grade filter for the depth filtration/clarification of whole milk.
Figure 5:
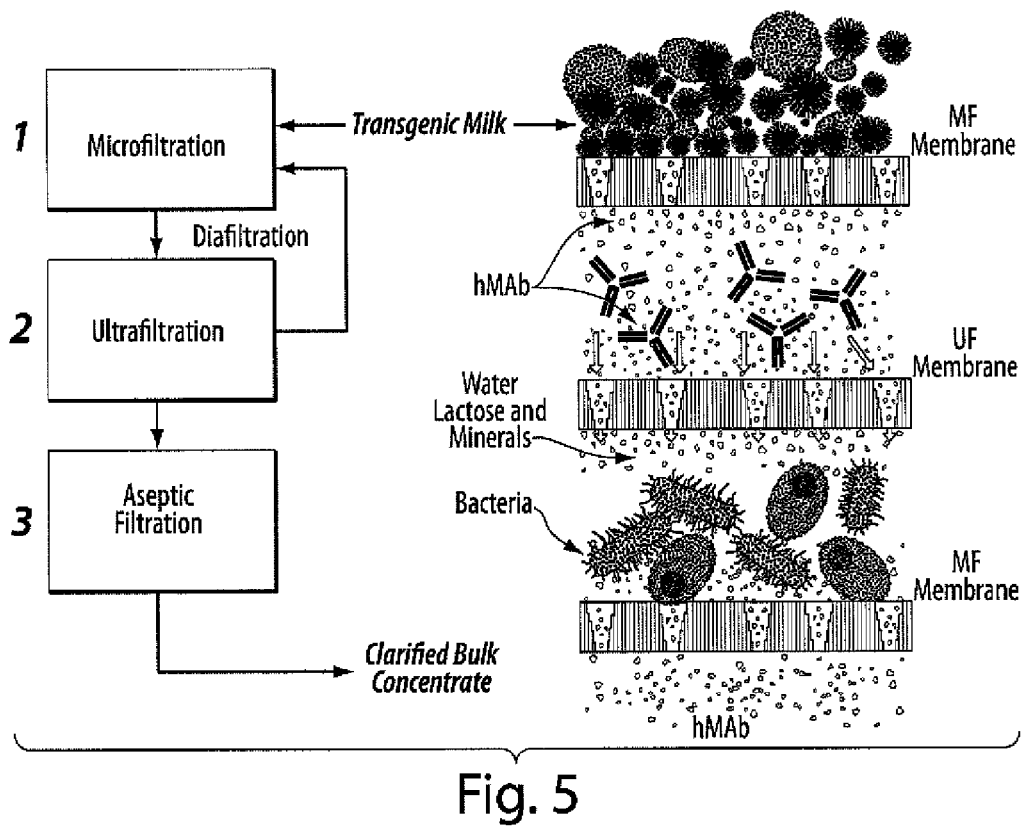
FIG. 5 Shows full Filtration Process Flow Diagram through microfiltration, ultrafiltration and final aseptic filtration. Depth Filtration would occur in the microfiltration step.
Figure 6:
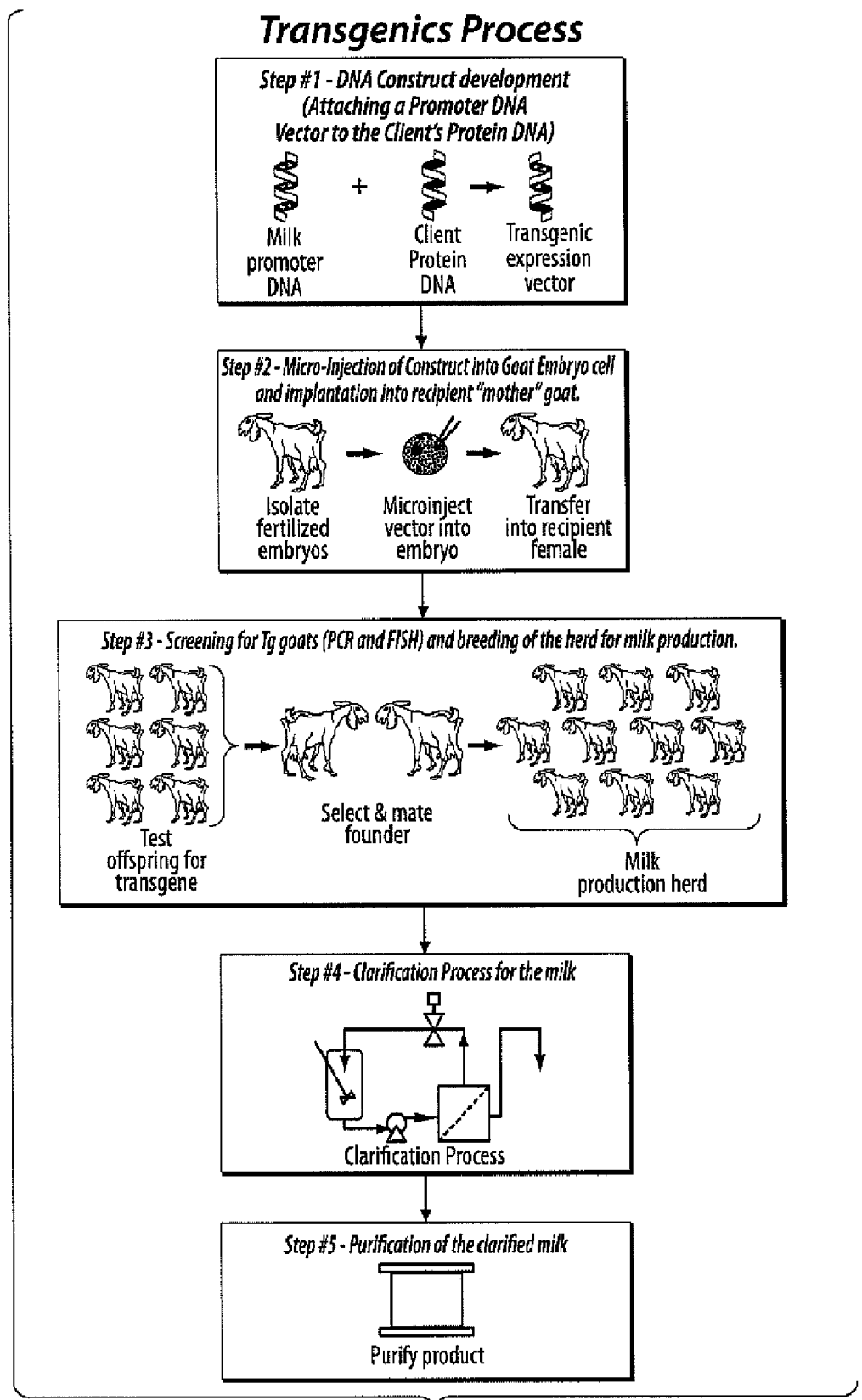
FIG. 6 Shows the process of generating a transgenic animal capable of producing a protein of interest in their milk.
Figure 7:
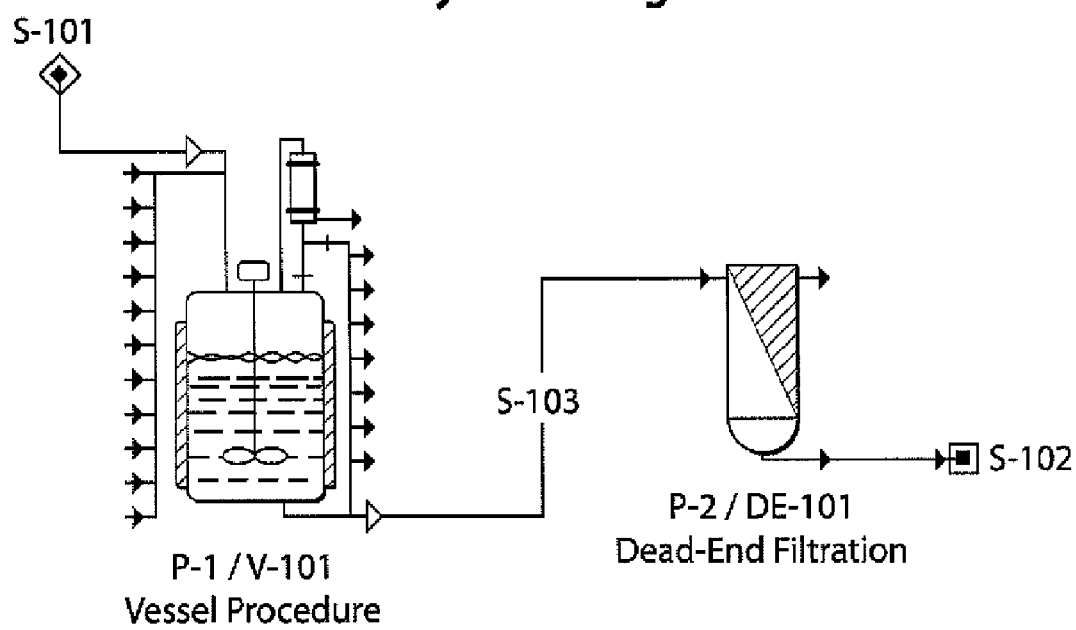
FIG. 7 Shows a DF System Diagram.
Figure 8:
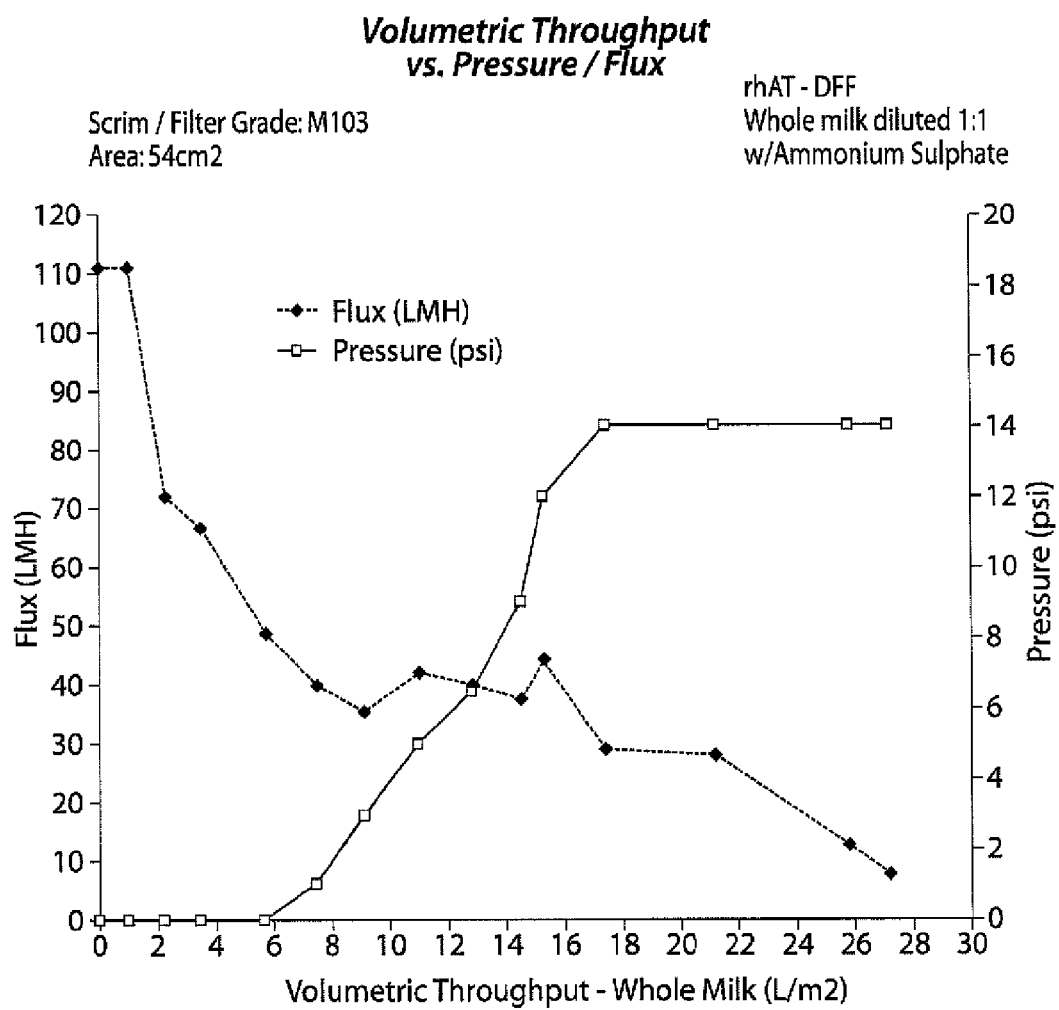
FIG. 8 Shows a Depth Filtration graph of rhAT of Volumetric Throughput versus Resistance with a M103 (10 μm) filter.
Figure 9:
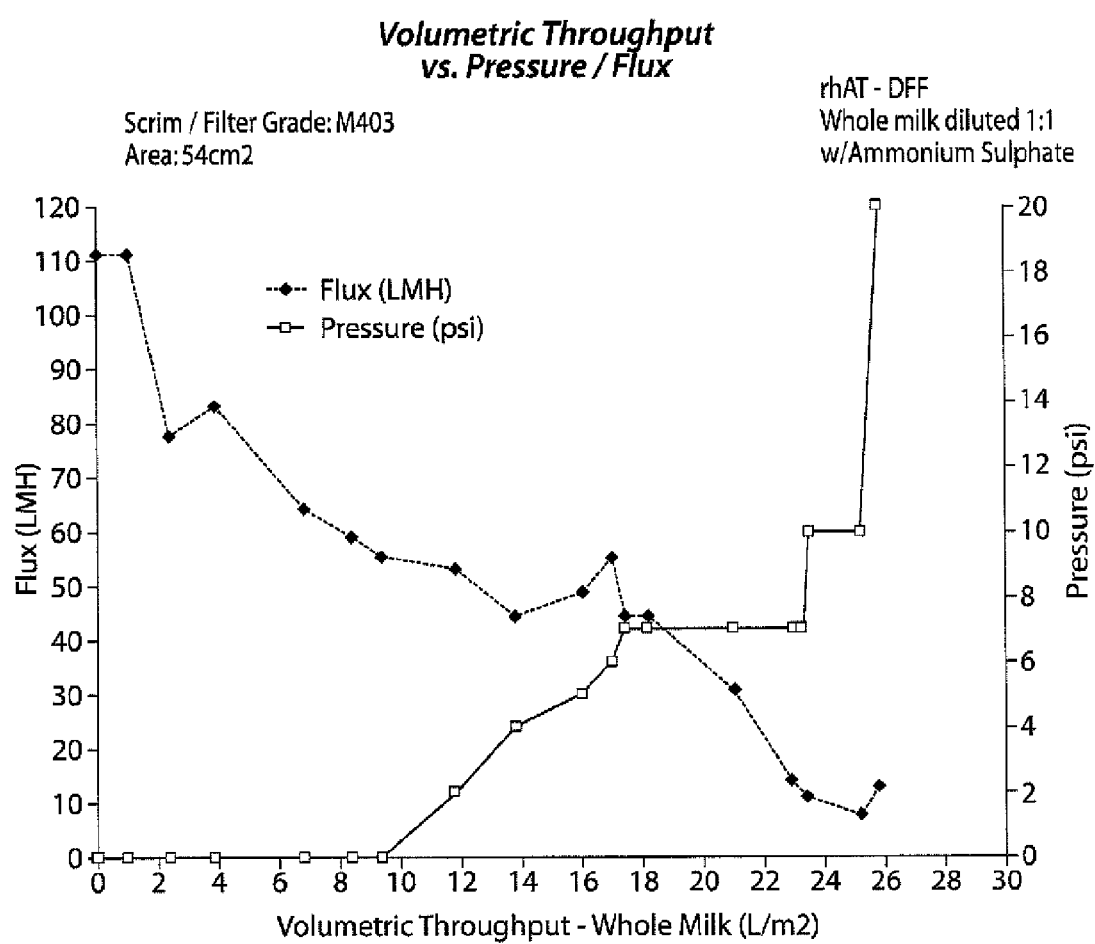
FIG. 9 Shows a Depth Filtration graph of rhAT of Volumetric Throughput versus Resistance with a M453 (2.5 μm) filter.
Figure 10:
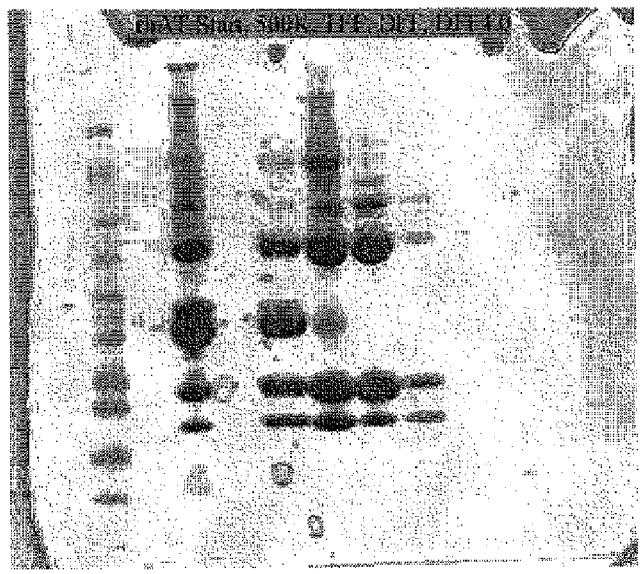
FIG. 10 Shows an SDS gel of rhAT compared to a Dual TFF filtration run.
Figure 11:
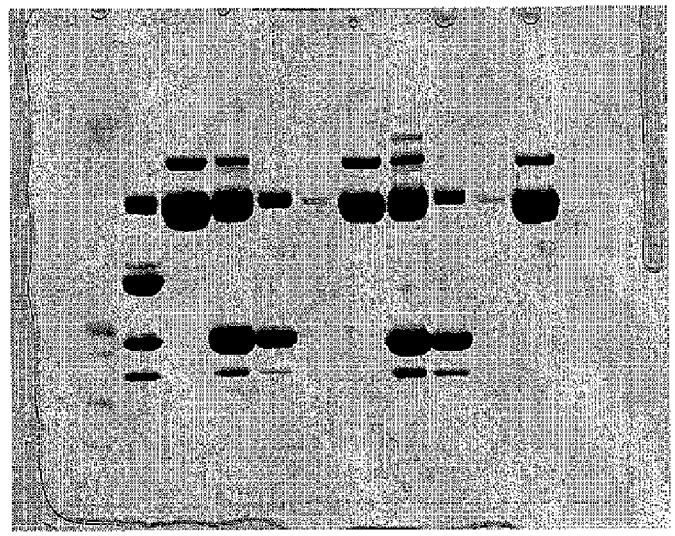
FIG. 11 Shows an SDS gel of rhAT from a TFF experiment and two different DF experiments, one control and one heat treated.
Figure 12A:
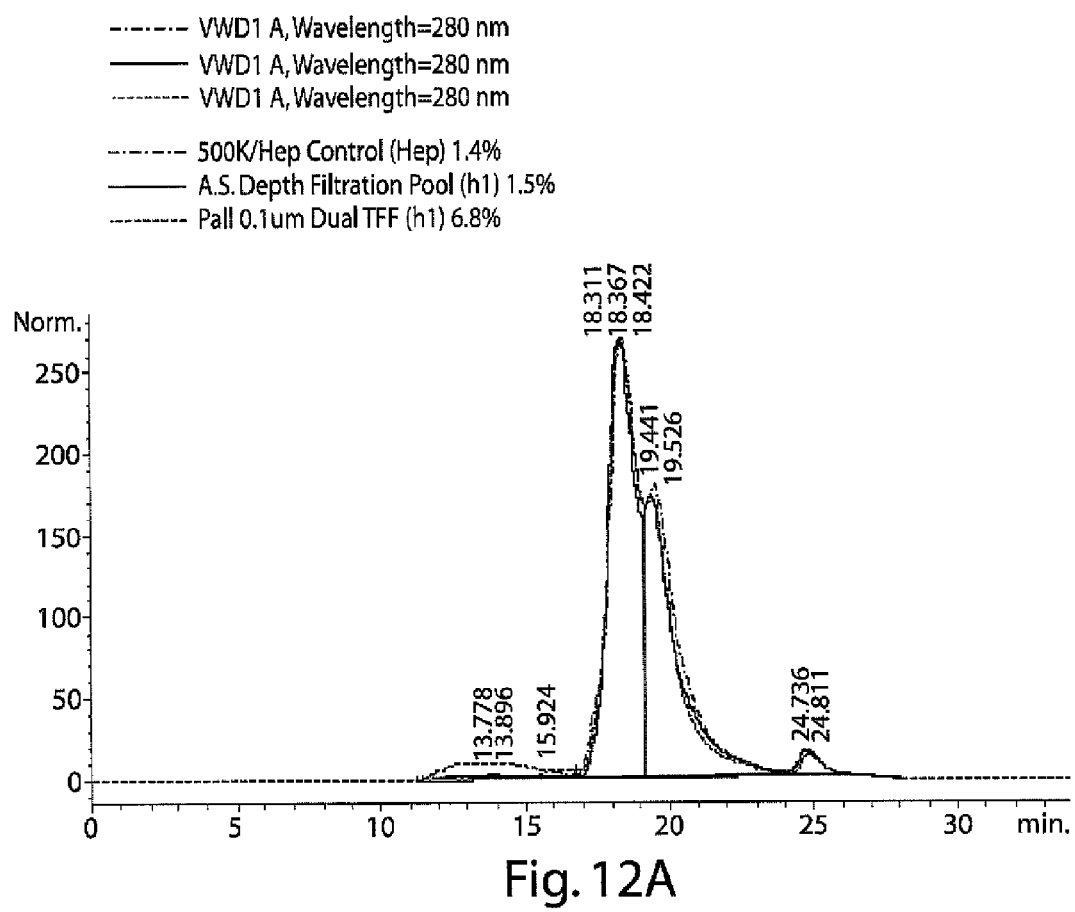
FIGS. 12A-12B Shows a SEC Chromatogram of Recovered rhAT.
Figure 12B:
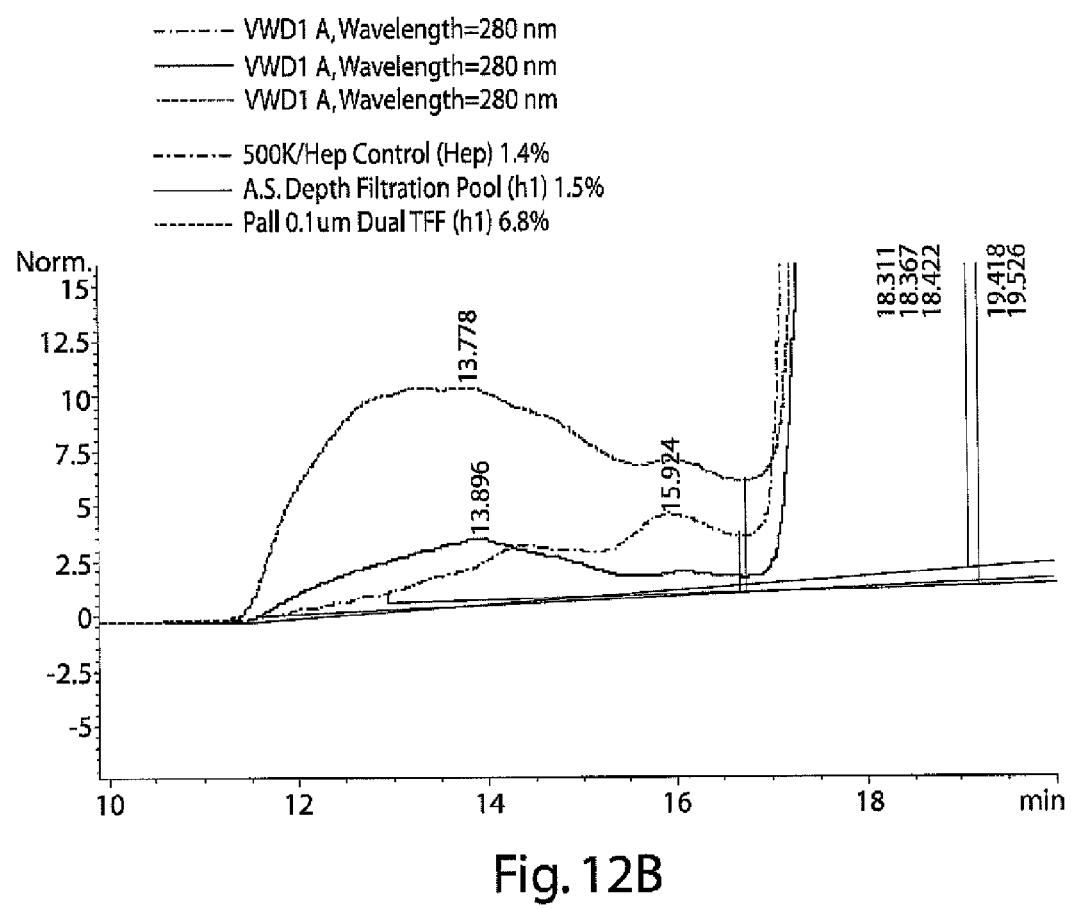
Figure 13:
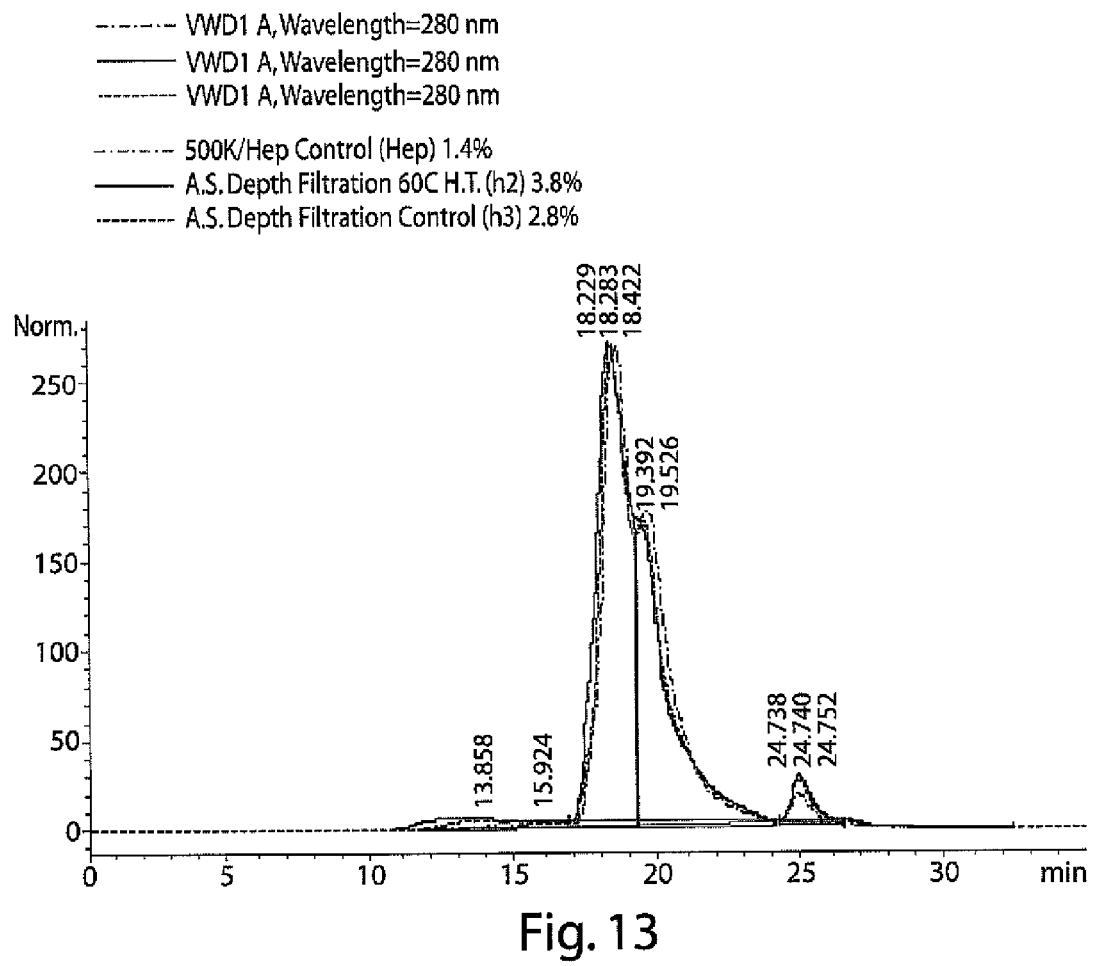
FIG. 13 Shows an enlarged portion of the SEC Chromatogram of DF recovered rhAT Compared to Alternative Methods.
Figure 14:
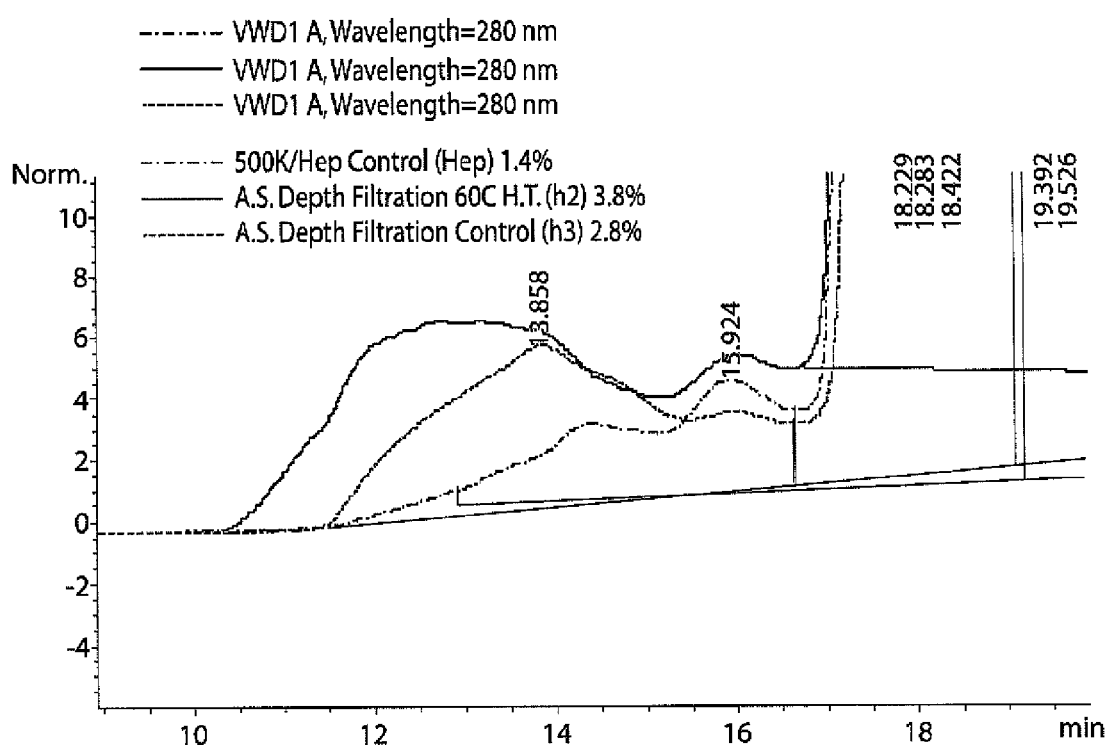
FIG. 14 Shows a SEC Chromatogram of DF Recovered rhAT Compared to Alternative MF TFF Methods.

Turning to FIG. 4, once the M403 (5.0 μm) grade filter was chosen for the depth filtration/clarification of whole milk, several batches were pooled, concentrated, and diafiltered using a 30 kD ultrafiltration membrane. This pooled sample was then purified using a 16 ml heparin column. Clarified milk from the present 500K clarification and 0.1 um dual TFF process were compared as well. In FIG. 11, the SDS PAGE shows that lanes 2, 7, and 11 contain the purified rhAT elution fraction. As can be seen each is similar in composition with the exception of lane 11 where aggregate can be seen. This aggregate was most evident in the 0.1 um dual TFF sample.

It has been shown in the data for the invention provided herein that clarification using depth filtration is feasible and can optimize the purification of several molecules from a milk feedstream. It is noted that according to preferred embodiments of the current invention the processes are scalable, inexpensive, and have a sustained high product yield (>90%).

Other data indicate that scale up from the 90 mm disk to a 1.1 ft$^2$ lenticular cartridge enhances the efficiency of the overall process. This cartridge will have the potential to clarify 3 liters of whole milk.

Milk Processing

According to the methods of the current invention it is preferable if the temperature of the milk is raised to 15-25° C. after it is pooled. The milk is pooled in a reservoir and an equal volume of salt buffer is prepared in a second reservoir. Next the two reservoirs are connected to a pump and in line static mixer. Once the feed stream line is connected to the filter element, the pump is turned on blending the milk and buffer prior to filtration. The use of the static mixer is significant as the mixing and resonance time is uniform throughout the entire filtration. Mixing the milk and buffer in a bulk tank prior to filtration is less desirable as the time that the mixture rests prior to filtration is variable. The pump is adjusted to the desired flow rate based on the average flux of 50 LMH. After 5 minutes the initial permeate sample(s) are taken and the critical pressures and flow rates are verified. The DF is run at 50 LMH with less than 15 psi of transmembrane pressure throughout the filtration. The temperature of the milk should remain at 20° C.±5. Once the entire volume of milk and buffer are consumed a volume of buffer, equal to 10% of the starting milk volume, is flushed through the filter to ensure the majority of the soluble protein is passed to the permeate.

Once filtration is complete, the permeate collection vessel is disconnected, the filters are disposed of, and the system is drained and cleaned. The DF clarified permeate is aseptically filtered, and stored at 4° C. prior to downstream purification.

Transgenic Animal Production

Other issues affect the overall yield of any manufacturing process involving transgenic mammals: stability of constructs, control of expression, and seasonal variations in lactation, to name a few. A sound understanding of the health and physiology of the livestock species used is essential because a transgenic animal may live for 7-10 years and will experience physiological changes and various environments throughout its life as it develops, gives birth, and ultimately lactates. Recovery processes must be robust enough to handle those changes, but if the advances in our understanding of milk composition and bioprocessing techniques continue, such challenges should be overcome as well.

According to the current invention, to extract a molecule of interest out of a given feedstream in preparation for use by an end use could be concluded with a series of additional purification steps. In general, a multiple stage process is preferable but not required. An exemplary two or three-stage process would consist of a coarse filter(s) to remove large precipitate and cell debris followed by polishing second stage filter(s) to with nominal pore sizes greater than 0.2 micron but less than 1 micron. The optimal combination will be a function of the precipitate size distribution as well as other variables. In addition, single stage operations employing a relatively tight filter or centrifugation may also produce a product of good quality. More generally, any clarification approach including dead-end filtration, microfiltration, centrifugation, or body feed of filter aids (e.g. diatomaceous earth) in combination with dead-end or depth filtration, which provides a filtrate of suitable clarity to not foul the membrane and/or resin in the subsequent steps, will be acceptable to practice within the present invention.

Cleaning and Storing Protocols

Cleaning the DF filters is not required as they are disposable; one of the obvious advantages over re-usable systems that require a large volume of cleaning solution and water. Once the filtration is complete the filter elements are removed and discarded. The filter housing, feed vessel, and pump are then the only components requiring cleaning. A thirty (30) minute cycle of 0.5 M sodium hydroxide followed by 0.3 M citric acid have proven to be effective when cleaning stainless steel components in the dairy industry. Once the cleaning cycle is complete, the components are rinsed with water and the filters are re-installed prior the next use.

Recombinant Production

A growing number of recombinant proteins are being developed for therapeutic and diagnostic applications. However, many of these proteins may be difficult or expensive to produce in a functional form and/or in the required quantities using conventional methods. Conventional methods involve inserting the gene responsible for the production of a particular protein into host cells such as bacteria, yeast, or mammalian cells, e.g., COS or CHO cells, and then growing the cells in culture media. The cultured cells then synthesize the desired protein. Traditional bacteria or yeast systems may be unable to produce many complex proteins in a functional form. While mammalian cells can reproduce complex proteins, they are generally difficult and expensive to grow, and often produce only mg/L quantities of protein. In addition, non-secreted proteins are relatively difficult to purify from procaryotic or mammalian cells as they are not secreted into the culture medium.

In general, the transgenic technology features, a method of making and secreting a protein which is not normally secreted (a non-secreted protein). The method includes expressing the protein from a nucleic acid construct which includes:

(a) a promoter, e.g., a mammary epithelial specific promoter, e.g., a milk protein promoter;

(b) a signal sequence which can direct the secretion of a protein, e.g. a signal sequence from a milk specific protein;

(c) optionally, a sequence which encodes a sufficient portion of the amino terminal coding region of a secreted protein, e.g., a protein secreted into milk, to allow secretion, e.g., in the milk of a transgenic mammal, of the non-secreted protein; and (d) a sequence which encodes a non-secreted protein, wherein elements (a), (b), optionally (c), and (d) are preferably operatively linked in the order recited.

In preferred embodiments: elements a, b, c (if present), and d are from the same gene; the elements a, b, c (if present), and d are from two or more genes.

In preferred embodiments the secretion is into the milk of a transgenic mammal.

In preferred embodiments: the signal sequence is the β-casein signal sequence; the promoter is the β-casein promoter sequence.

In preferred embodiments the non-secreted protein-coding sequence: is of human origin; codes for a truncated, nuclear, or a cytoplasmic polypeptide; codes for human serum albumin or other desired protein of interest.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for an improved method of depth filtration to generate a high yield of a molecule of interest from a given feedstream are merely illustrative of the application of the principles of the invention. It will be evident from the foregoing description that changes in the form, methods of use, and applications of the elements of the disclosed may be resorted to without departing from the spirit of the invention, or the scope of the appended claims.

PRIOR ART CITATIONS INCORPORATED BY REFERENCE

1. Aravindan G R, et al., (1997), *Identification, Isolation, and Characterization Of A 41-Kilodalton Protein From Rat Germ Cell-Conditioned Medium Exhibiting Concentration-Dependent Dual Biological Activities*, ENDOCRINOLOGY 138(8):3259-68.

2. Bracewell D. G. et al., (2004) *Addressing a Whole Bioprocess in Real-Time Using an Optical Biosensor-Formation, Recovery and Purification of Antibody Fragments From a Recombinant E. Coli Host*, BIOPROCESS BIOSYST ENG. 2004 July; 26(4):271-82. Epub 2004 May 5.

3. Charlton H. R., et al., (1999) *Characterization of a Generic Monoclonal Antibody Harvesting System for Adsorption of DNA by Depth Filters and Various Membranes*, BIOSEPARATION. 8(6):281-91.

4. Christy C., et al., (2002) *High Performance Tangential Flow Filtration: A Highly Selective Membrane Separation Process*, DESALINATION, vol. 144: 133-36.

5. De Jonge, E. et al. (1993), *Filtration Processes in the Cohn Fractionation Process*. BIOTECHNOL BLOOD PROTEINS, 227:49-54.

6. Gabler et al., (1987), *Principles of Tangential Flow Filtration: Applications to Biological Processing*, in FILTRATION IN THE PHARMACEUTICAL INDUSTRY, pp. 453-490.

7. Ghosh R, et al., (2003) *Parameter Scanning Ultrafiltration: Rapid Optimisation of Protein Separation*, BIOTECHNOL BIOENG., March 20; 81(6):673-82.

8. Koros, W. J. et al., (1996), *Terminology for Membranes and Membrane Processes* (IUPAC Recommendations 1996). PURE & APPL. CHEM. 68: 1479-89.

9. Millesime L, et al., (1996) *Fractionation of Proteins with Modified Membranes*, BIOSEPARATION, June; 6(3):135-45.

10. Morcol et al., *Model Process for Removal of Caseins from Milk of Transgenic Animals*, BIOTECHNOL. PROG. 17:577-82 (2001).

11. Prado S M, et al., (1999), *Development and Validation Study for the Chromatographic Purification Process for Tetanus Anatoxin on Sephacryl S-200 High Resolution*, BOLL CHIM FARM. 138(7):364-368.

12. Porter, ed., HANDBOOK OF INDUSTRIAL MEMBRANE TECHNOLOGY, (Noyes Publications, Park Ridge, N.J., (1998)) pp. 160-176.

13. Ramachandra-Rao, H. G. et al., (2002) *Mechanisms of Flux Decline During Ultrafiltration of Dairy Products and Influence of pH on Flux Rates of Whey and Buttermilk*, DESALINATION, vol. 144: 319-24.

14. Reynolds, T. et al., (2003) *Scale-Down of Continuous Filtration for Rapid Bioprocess Design: Recovery and Dewatering of Protein Precipitate Suspensions*, BIOTECHNOL. BIOENG. August 20; 83(4):454-64

15. Van Holten R. W. et al., (2003), *Evaluation of Depth Filtration to Remove Prion Challenge from an Immune Globulin Preparation*, VOX SANG. July; 85(1):20-4.

16. Van Reis R., and Zydney A., *Review*, CURR OPIN BIOTECHNOL., (2001) April; 12(2):208-11.

17. Zeman, L. J. & Zydney, A. L. (1996), *Microfiltration and Ultrafiltration*, in PRINCIPLES AND APPLICATIONS. (Marcel Dekker ed.), New York.

UNITED STATES PATENTS AND INTERNATIONAL PATENTS INCORPORATED BY REFERENCE

1. Antonsen, K P et al., U.S. Pat. No. 6,194,553, PURIFICATION OF ALPHA-1 PROTEINASE INHIBITOR.
2. Jain M. et al., U.S. Pat. No. 4,351,710, FRACTIONATION OF PROTEIN MIXTURES.
3. Kothe et al., U.S. Pat. No. 4,644,056, METHOD OF PREPARING A SOLUTION OF LACTIC OR COLOSTRIC IMMUNOGLOBULINS OR BOTH AND USE THEREOF
4. Sandblom R. M. et al., U.S. Pat. No. 4,105,547, FILTERING PROCESS.
5. Sherman, L. T. et al., U.S. Pat. No. 6,268,487, PURIFICATION OF BIOLOGICALLY ACTIVE PEPTIDES FROM MILK.
6. Udell, M. et al., European Patent No.: EP1115745 (WO0017239), PURIFICATION OF FIBRINOGEN FROM FLUIDS BY PRECIPITATION AND HYDROPHOBIC CHROMATOGRAPHY.
7. Van Reis R. M., et al., U.S. Pat. No. 6,555,006, TANGENTIAL-FLOW FILTRATION SYSTEM.
8. Van Reis R. M., et al., U.S. Pat. No. 6,221,249, TANGENTIAL-FLOW FILTRATION SYSTEM.
9. Van Reis R. M., et al., U.S. Pat. No. 6,054,051, TANGENTIAL-FLOW FILTRATION SYSTEM.
10. Van Reis R. M., et al., U.S. Pat. No. 5,490,937, TANGENTIAL FLOW FILTRATION PROCESS AND APPARATUS.
11. Van Reis R. M., et al., U.S. Pat. No. 5,256,294, TANGENTIAL FLOW FILTRATION PROCESS AND APPARATUS.

What is claimed is:

1. A method for separating a protein of interest from a feedstream, comprising:
    filtering said feedstream by a depth filtration process that separates a protein of interest from said feedstream on the basis of particulate size,
    wherein said feedstream containing the protein of interest is composed of milk from a transgenic mammal,
    wherein milk casein micelles are aggregated by dilution with an ammonium sulfate solution, and
    wherein the feedstream and the ammonium sulfate solution are blended prior to filtration by an in line static mixer in fluid communication with a filtration element of said depth filtration process.

2. The method of claim 1, wherein the depth filtration process comprises a filter matrix capable of trapping particles in the range of about 1-5 microns.

3. The method of claim 1, wherein the depth filtration process comprises a filter matrix capable of trapping particles ranging from 5 microns to 50 microns.

4. The method of claim 1 wherein the depth filtration process comprises a filter matrix capable of trapping particles ranging from 10 microns to 25 microns.

5. The method of claim 1, further comprising dissociating the milk casein micelles from the rest of the feedstream through the use of EDTA.

6. The method of claim 1, further comprising wherein at least 3 liters/ft2 of feedstream containing a protein of interest can be processed in 2 hours at 60 LMH.

7. The method of claim 1, further comprising wherein 3 liters/ft2 of feedstream containing a protein of interest can be processed in 2-4 hours at 30-60 LMH.

8. The method of claim 1, wherein the depth filtration process comprises a filter medium composed of one or more of the following materials: metallic, polymeric, inorganic, or organic materials.

9. The method of claim 1, wherein said protein of interest has a molecular weight of between 1 and 1000 kDa.

10. The method of claim 1, wherein said feedstream is diluted before depth filtration.

11. The method of claim 1, wherein said protein of interest is bioactive.

12. The method of claim 1, wherein the condition of said milk is selected from the group consisting of:
    a) raw;
    b) diluted;
    c) treated with a buffer solution;
    d) chemically treated; and
    e) concentrated.

13. The method of claim 1, wherein the depth filtration process is carried out at a permeation flux of less than 30 lmh.

14. The method of claim 1, wherein the depth filtration process is carried out at a pH above that at which said protein of interest does not precipitate.

15. The method of claim 1, further comprising a fractionation step utilizing a cellulose filtration membrane.

16. The method of claim 1 wherein said protein of interest is a biological entity selected from the group consisting of proteins, immunoglobulins, polypeptides, peptides and glycoproteins.

17. The method of claim 1, wherein the depth filtration is performed at a temperature of 4° C. to 40° C.

18. The method of claim 17, wherein the depth filtration is performed at a temperature of 15° C. to 30° C.

19. The method of claim 18, wherein the depth filtration is performed at a temperature of 20° C. to 25° C.

20. The method of claim 1, further comprising after the filtering step an anion chromatography step.

21. The method of claim 1, further comprising after the filtering step a cation chromatography step.

22. The method of claim 1, further comprising after the filtering step a size exclusion chromatography step.

23. The method of claim 1, further comprising after the filtering step a reverse phase chromatography step.

24. The method of claim 1, wherein the feedstream has a concentration ranging from 0.25×to 4×natural milk.

25. The method of claim 1, wherein the feedstream has a concentration ranging from 0.5×to 3×natural milk.

26. The method of claim 1, wherein the depth filtration process is carried out at the protein of interest's isoelectric pH.

27. The method of claim 1, wherein the protein of interest is selected from the group consisting of alpha-1-antitrypsin, alkaline phosphatase, angiogenin, antithrombin, chitinase, extracellular superoxide dismutase, Factor VIII, Factor TX, Factor X, fibrinogen, glucocerebrosidase, glutamate decarboxylase, human serum albumin, insulin, myelin basic protein, lactoferrin, lactoglobulin, lysozyme, lactalbumin, proinsulin, soluble CD4, component and complex of soluble CD4, and tissue plaminogen activator.

28. The method of claim 1, wherein said feedstream is treated with a solution selected from the group consisting of:
a) water;
b) a buffered aqueous salt solution;
c) chelating agent;
d) acid solution; and
e) alkali solution.

* * * * *